US006949584B2

(12) United States Patent
Satchi-Fainaro et al.

(10) Patent No.: US 6,949,584 B2
(45) Date of Patent: Sep. 27, 2005

(54) TNP-470 SPECIES, POLYMER CONJUGATES AND USE THEREOF

(75) Inventors: Ronit Satchi-Fainaro, Chestnut Hill, MA (US); Judah Folkman, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 10/783,986

(22) Filed: Feb. 19, 2004

(65) Prior Publication Data

US 2004/0229945 A1 Nov. 18, 2004

Related U.S. Application Data

(63) Continuation-in-part of application No. PCT/US03/10976, filed on Apr. 10, 2003.
(60) Provisional application No. 60/371,791, filed on Apr. 11, 2002, and provisional application No. 60/414,705, filed on Sep. 30, 2002.

(51) Int. Cl.$^7$ .................... C07D 407/08; A61K 31/336; A61P 35/04

(52) U.S. Cl. ...................................... 514/475; 549/332

(58) Field of Search .......................... 514/475; 549/332

(56) References Cited

U.S. PATENT DOCUMENTS

| | | | |
|---|---|---|---|
| 5,164,410 A | 11/1992 | Kishimoto et al. | |
| 5,166,172 A | 11/1992 | Kishimoto et al. | |
| 5,180,735 A | 1/1993 | Kishimoto et al. | |
| 5,180,738 A | * 1/1993 | Kishimoto et al. | ......... 514/475 |
| 5,290,807 A | 3/1994 | Folkman et al. | |
| 5,698,586 A | 12/1997 | Kishimoto et al. | |
| 6,017,954 A | 1/2000 | Folkman et al. | |
| 6,022,888 A | 2/2000 | Morishige et al. | |
| 6,225,478 B1 | 5/2001 | Morishige et al. | |
| 2003/0109671 A1 | 6/2003 | Olson et al. | |

OTHER PUBLICATIONS

Folkman, J., Angiogenesis, in *Harrison's Textbook of Internal Medicine* (eds. Braunwald, E. et al.) 517–530 (McGraw Hill, New York, 2001).
Hanahan, D. et al., Patterns and emerging mechanisms of the angiogenic switch during tumorigenesis, *Cell*, 86:353–64 (1996).
Volpert, O.V. et al., Id1 regulates angiogenesis through transcriptional repression of thrombospondin–1, *Cancer Cell*, 2:473–483 (2002).
Folkman, J., Tumor angiogenesis, *Cancer Medicine* (eds. Holland, J. et al.), pp. 132–152 (B. C. Decker Inc., Ontario, Canada, 2000).
Lyden, D. et al., Id1 and Id3 are required for neurogenesis angiogenesis and vascularization of tumour xenografts, *Nature*, 401:670–677 (1999).

Streit, M. et al., Thrombospondin–2: a potent endogenous inhibitor of tumor growth and angiogenesis, *Proc. Natl. Acad. Sci. USA*, 96:14888–14893 (1999).
Chin, L. et al., Essential role for oncogenic Ras in tumour maintenance, *Nature*, 400:468–472 (1999).
Tabone, M.D. et al., Are basic fibroblast growth factor and vascular endothelial growth factor prognostic indicators in pediatric patients with malignant solid tumors?, *Clinical Cancer Res.*, 7:538–543 (2001).
Yao, Y. et al., Prognostic value of vascular endothelial growth factor and its receptors Flt–1 and Flk–1 in astrocytic tumours, *Acta Neurochir (Wien)*, 143:159–66 (2001).
Yuan, A. et al., Aberrant p53 expression correlates with expression of vascular endothelial growth factor mRNA and interleukin–8 mRNA and neoangiogenesis in non–small–cell lung cancer, *J. Clinical Oncology*, 20:900–910 (2002).
Ingber, D. et al., Synthetic analogues of fumagillin that inhibit angiogenesis and suppress tumour growth, *Nature*, 348:555–557 (1990).
Antoine, N. et al., AGM–1470, a potent angiogenesis inhibitor, prevents the entry of normal but not transformed endothelial cells into the $G_1$ phase of the cell cycle, *Cancer Res.*, 54:2073–2076 (1994).
Kudelka, A.P. et al., Complete remission of metastatic cervical cancer with the angiogenesis inhibitor TNP–470, *N. Engl. J. Med.*, 338:991–2 (1998).
Kudelka, A.P. et al., A phase I study of TNP–470 administered to patients with advanced squamous cell cancer of the cervix, *Clinical Cancer Res.*, 3:1501–1505 (1997).
Bhargava, P. et al., A Phase I and pharmacokinetic study of TNP–470 administered weekly to patients with advanced cancer, *Clinical Cancer Res.*, 5:1989–1995 (1999).
Herbst, R.S. et al., Safety and pharmacokinetic effects of TNP–470, an angiogenesis inhibitor, combined with paclitaxel in patients with solid tumors: evidence for activity in non–small–cell lung cancer, *J. Clinical Oncol.*, 20:4440–4447 (2002).
Kim, E.S. et al., Angiogenesis inhibitors in lung cancer. *Curr. Oncol. Rep.*, 4:325–333 (2002).
Stadler, W.M. et al., Multi–institutional study of the angiogenesis inhibitor TNP–470 in metastatic renal carcinoma, *J. Clinical Oncol.*, 17:2541–2545 (1999).

(Continued)

*Primary Examiner*—Venkataraman Balasubramanian
(74) *Attorney, Agent, or Firm*—Nixon Peabody LLP

(57) ABSTRACT

The present invention relates to conjugates of water-soluble polymers and o-(chloracetyl-carbamoyl) fumagillol (TNP-470) and use of those conjugates as specific intracellular carriers of the TNP-470 into tumor vessels. The present invention further relates to use of those conjugates to lower the neurotoxicity of TNP-470. Preferably, the polymer has a molecular weight in the range of 100 Da to 800 kDa. More preferably, the polymer has a molecular weight no greater than 60 kDa. Most preferably, the polymer has a molecular weight in the range of 15 kDa to 40 kDa.

3 Claims, 16 Drawing Sheets

OTHER PUBLICATIONS

Logothetis, C.J. et al., Phase I trial of the angiogenesis inhibitor TNP–470 for progressive androgen–independent prostate cancer, *Clinical Cancer Res.,* 7:1198–1203 (2001).

Rupnick, M.A. et al., Adipose tissue mass can be regulated through the vasculature, *Proc. Natl. Acad. Sci. U S A,* 99:10730–10735 (2002).

Schoof, D.D. et al., The influence of angiogenesis inhibitor AGM–1470 on immune system status and tumor growth in vitro, *Int. J. Cancer,* 55:630–635 (1993).

Nagabuchi, E. et al., TNP–470 antiangiogenic therapy for advanced murine neuroblastoma, *J. Pediatric Surg.,* 32:287–93 (1997).

Rihova, B. et al., Biocompatibility of N–(2–hydroxypropyl) methacrylamide copolymers containing adriamycin. Immunogenicity, and effect on haematopoietic stem cells in bone marrow in vivo and mouse splenocytes and human peripheral blood lymphocytes in vitro, *Biomaterials,* 10:335–342. (1989).

Seymour, L.W. et al., The pharmacokinetics of polymer–bound adriamycin, *Biochem. Pharmacol.,* 39:1125–1131 (1990).

Maeda, H. et al., Tumor vascular permeability and the EPR effect in macromolecular therapeutics: a review, *J. Controlled Release,* 65:271–284 (2000).

Duncan, R. et al., Preclinical toxicology of a novel polymeric antitumour agent: HPMA copolymer–doxorubicin (PK1), *Human and Exp. Toxicology,* 17:93–104 (1998).

Satchi–Fainaro, R., Targeting tumor vasculature: Reality or a dream?.*J. Drug Targeting,* 10:529–533 (2002).

Duncan, R. et al., Polymers containing enzymatically degradable bonds, 7. Design of oligopeptide side chains in poly [N–(2–hydroxypropyl)methacrylamide] copolymers to promote efficient degradation by lysosomal enzymes, *Makromol. Chem.,* 184:1997–2008 (1983).

Foekens, J.A. et al., Prognostic significance of cathepsins B and L in primary human breast cancer.*J. Clinical Oncol.,* 16:1013–1021 (1998).

Gianasi, E. et al., HPMA copolymer platinates as novel antitumour agents: in vitro properties, pharmacokinetics and antitumour activity in vivo, *Eur. J. Cancer,* 35:994–1002 (1999).

Kusaka, M. et al. Cytostatic inhibition of endothelial cell growth by the angiogenesis inhibitor TNP–470 (AGM–1470), *Br. J. Cancer.* 69:212–216 (1994).

Greene, A.K. et al., Endothelial–directed hepatic regeneration after partial hepatectomy, *Ann. Surg.,* 237:530–535 (2003).

Drixler, T.A. et al., Liver regeneration is an angiogenesis–associated phenomenon, *Ann. Surg.,* 236:703–712 (2002).

Klein, S.A. et al., Angiogenesis inhibitor TNP–470 inhibits murine cutaneous wound healing,*J. Surg. Res.,* 82:268–274 (1999).

Whalen, C.T. et al., Assay of TNP–470 and its two major metabolites in human plasma by high–performance liquid chromatography–mass spectrometry, *J. Chromatographic Sci.,* 40:214–218 (2002).

Brocchini, S. et al., Polymer–Drug conjugates: drug release from pendent linkers. in *Encyclopaedia of controlled release* (ed. Mathiovitz, E.) 786–816 (New York: Wiley, 1999).

Duncan, R. et al., Polymer–drug conjugates, PDEPT and PELT: basic principles for design and transfer from the laboratory to clinic, *J. Controlled Release,* 74:135–146 (2001).

Vasey, P.A. et al., Phase I clinical and pharmacokinetic study of PK1 [N–(2–hydroxypropyl)methacrylamide copolymer doxorubicin]: first member of a new class of chemotherapeutic agents–drug–polymer conjugates, Cancer Research Campaign Phase I/II Committee, *Clinical Cancer Res.,* 5:83–94 (1999).

Seymour, L.W. et al., Tumour tropism and anti–cancer efficacy of polymer–based doxorubicin prodrugs in the treatment of subcutaneous murine B16F10 melanoma, *Br. J. Cancer,* 70:636–641 (1994).

Dvorak, H.F. et al., Identification and characterization of the blood vessels of solid tumors that are leaky to circulating macromolecules. *Am. J. Pathology,* 133:95–109 (1988).

Griffith, E.C. et al., Methionine aminopeptidase (type 2) is the common target for angiogenesis inhibitors AGM–1470 and ovalicin, *Chem. and Biol.,* 4, 461–471 (1997).

Auerbach, R. et al., Angiogenesis assays: problems and pitfalls, *Cancer Metastasis Rev.,* 19:167–172 (2000).

Seymour, L.W. et al., Hepatic drug targeting: phase I evaluation of polymer–bound doxorubicin., *J. Clinical Oncol.,* 20:1668–1676 (2002).

Francis, G.E. et al., PEG–modified proteins. in *Stability of Proteins Pharmaceuticals (Part B)* (ed. Ahem Tj, M.M.) 235–263 (Plenum Press, New York, 1992).

Ho, D.H. et al., Clinical pharmacology of polyethylene glycol–L–asparaginase, *Drug Metabolism Disposition,* 14:349–352 (1986).

O'Reilly, M.S. et al., Angiostatin: a novel angiogenesis inhibitor that mediates the suppression of metastases by a Lewis lung carcinoma, *Cell,* 79:315–328 (1994).

Folkman, J. et al., Long–term culture of capillary endothelial cells, *Proc. Natl. Acad. Sci. USA,* 76:5217–5221 (1979).

Waynforth, H.B. Routes and methods of administration, Intracerebral injection. in *Experimental and Surgical technique in the rat,* vol. 2.9 34–36 (Academic Press, London, 1980).

Seymour, L.W. et al., The pharmacokinetics of polymer–bound adriamycin, *Biochemical Pharmacology,* 39:1125–1131 (1990).

Yeh, J.R. et al., The antiangiogenic agent TNP–470 requires p53 and p21$^{CIP/WAF}$ for endothelial cell growth arrest, *Proc. Natl. Acad. Sc.i USA,* 97:12782–12787 (2000).

Zhang, Y. et al., Cell cycle inhibition by the anti–angiogenic agent TNP–470 is mediated by p53 and p21$^{WAF1/CIP1}$, *Proc. Natl. Acad. Sci. USA,* 97:6427–6432 (2000).

Seymour, L.W. et al., N–(2–hydroxypropyl) methacrylamide copolymers targeted to the hepatocyte galactose–receptor: pharmacokinetics in DBA$_2$ mice, *Br. J. Cancer,* 63:859–866 (1991).

Folkman, J. Tumor angiogenesis. in *Accomplishments in cancer research* (eds. Wells, S.J. & Sharp, P.) 32–44 (Lippincott Williams & Wilkins, New York, 1998).

\* cited by examiner

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      linker sequence

<400> SEQUENCE: 1

Gly Phe Leu Gly
1

TNP-470 SPECIES, POLYMER CONJUGATES AND USE THEREOF

CROSS-REFERENCE

This application is a Continuation-in-Part of International Application No. PCT/US03/10976 filed on Apr. 10, 2003, designating the United States, which claims benefit under 35 U.S.C. § 119(e) to U.S. Provisional Application Nos. 60/371,791 filed Apr. 11, 2002 and 60/414,705 filed on Sep. 30, 2002.

BACKGROUND OF THE INVENTION

In recent years, it has become clear that angiogenesis, the growth of new capillary blood vessels from pre-existing vasculature, is important not only in physiological processes such as embryonic development, the female reproductive cycle, wound healing, and organ and tissue regeneration, but also in pathological processes such as tumor progression and metastasis[1]. Angiogenesis is now recognized as a critical process for all malignancies[2,3]. As a result, the microvascular endothelial cell, which is recruited by tumors, has become an important second target in cancer therapy. It is widely accepted that the endothelial cell target, unlike the tumor cells themselves is genetically stable[1]. Antiangiogenic agents have recently emerged as a new class of drugs; however, the optimal means to use these agents alone or in combination with drug delivery systems and with conventional chemotherapy have not yet been fully elucidated.

The hypothesis that tumor growth is angiogenesis-dependent is supported by biological and pharmacological evidence[4] and confirmed by genetic evidence[3,5-7]. Both types of evidence provide a scientific basis for current clinical trials of angiogenesis inhibitors. Increased tumor angiogenesis[4,8] and elevated levels of proangiogenic factors such as vascular endothelial growth factor (VEGF/VPF)[8,9], basic fibroblast growth factor (bFGF)[8], and interleukin-8 (IL-8)[10] correlate with decreased survival and increased risk of relapse in studies of patients with malignant solid tumors. The importance of angiogenesis is further supported by the observation that antiangiogenic agents inhibit tumor growth in a variety of animal models.

In the U.S. there are currently more than 30 angiogenesis inhibitors in various clinical trials for late-stage cancer. One of these angiogenesis inhibitors, O-(chloracetyl-carbamoyl) fumagillol (TNP-470), is a low molecular weight synthetic analogue of fumagillin[11], a compound secreted by the fungus Aspergillus fumigatus fresenius. TNP-470 is a potent endothelial inhibitor in vitro[12]. Recently, TNP-470 has been tested as a potential new anticancer agent. In animal models, TNP-470 has the broadest anticancer spectrum of any known agent[4,13]. TNP-470 inhibited the growth of murine tumors up to 91%, human tumors up to 100% and metastatic tumors up to 100% in mice (reviewed in ref. [13]) In most studies, mice were treated at the same optimal dose of 30 mg/kg subcutaneously every other day. In clinical trials TNP-470 has shown evidence of antitumor activity when used as a single agent, with a number of objective responses reported with relapsed and refractory malignancies[14-16]. It has also shown promise when used in combination with conventional chemotherapy[17,18]. However, many patients experience neurotoxicity (malaise, rare seizures, asthenia, anxiety and dysphoria)[16,17,19,20] at doses where antitumor activity has been seen. Because of dose-limiting neurotoxicity, TNP-470 has been tested using multiple dosing regimens, but these attempts to limit its toxicity have been unsuccessful. With few exceptions, weight loss or failure to gain weight was observed in animals receiving TNP-470[21], and two reports noted a decrease in splenic weight[22,23]. Therefore, modifications of TNP-470 that can retain or increase its activity while reducing its toxicity are highly desirable.

SUMMARY OF THE INVENTION

The present invention relates to conjugates of water-soluble polymers and o-(chloracetyl-carbamoyl) fumagillol (TNP-470) and use of those conjugates as specific intracellular carriers of the TNP-470 into tumor vessels. This invention also relates to an intermediate formed in the synthesis of these conjugates and its use. The present invention further relates to use of those conjugates to lower the neurotoxicity of TNP-470. Preferably, the polymer has a molecular weight in the range of 100 Da to 800 kDa. More preferably, the polymer has a molecular weight no greater than 60 kDa. Most preferably, the polymer has a molecular weight in the range of 15 kDa to 40 kDa.

Preferred polymers are HPMA copolymers. HPMA copolymers are biocompatible, non-immunogenic and non-toxic carriers that enable specific delivery into tumor endothelial cells overcoming limitations of drug-related toxicities (Duncan, et al., Hum Exp Toxicol, 17:93–104 (1998)). Moreover, their body distribution is well characterized and they are known to accumulate selectively in the tumor site due to the enhanced permeability and retention (EPR) effect (Maeda, et al., J Controlled Release, 65:271–284 (2000)). The conjugate can also include a targeting moiety to direct the conjugate to sites of endothelial cell proliferation or cancer cells or to specific receptors or markers associated with proliferating endothelial cells.

TNP-470 can be conjugated to a polymer via nucleophelic attack on the α-carboxyl releasing the chlorine. The intermediate formed has the pertinent structure,

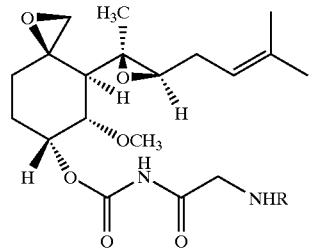

wherein R is $(CH_2)_n R'$, where n is 0 to 3, R' is $NH_2$, O or S.

The TNP-470 conjugate when cleaved enzymatically forms the above described structure wherein R is $(CH_2)_2 NH_2$.

This intermediate, or a pharmaceutically acceptable salt thereof, can also be used as an anti-tumor agent. It, like the polymer conjugate, is antiangiogenic and would also form the active TNP-470 metabolite.

The data presented herein demonstrate that, for example, TNP-470 conjugated to an HPMA copolymer: (i) avoid high peak drug levels in the circulation (ii) avoid penetration of TNP-470 to the cerebrospinal fluid and thus prevent the problem of neurotoxicity; (iii) prolong its half-life; (iv) facilitate the accumulation of TNP-470 in tissues involving neovascularization; (v) convert TNP-470 to a highly effective and widely useful angiogenesis inhibitor. We have also surprisingly discovered that conjugating TNP-470 to HPMA results in a water soluble composition.

The present invention further relates to use of the conjugates in methods of treating angiogenic diseases and decreasing neurotoxicity of TNP-470. Angiogenic disease amenable to treatment with the present invention include but are not limited to diabetic retinopathy, macular degeneration, retrolental fibroplasia, trachoma, neovascular glaucoma, psoriases, angio-fibromas, immune and non-immune inflammation, capillary formation within atherosclerotic plaques, hemangiomas, excessive wound repair, solid tumors, metastases, Kaposi's sarcoma and the like.

In accordance with the present invention, if polymer a having a molecular weight greater than 60 kDa is used, it is preferred that the polymer be a degradable polymer or inert. As used herein, a "degradable" polymer is one that breaks down in vivo to components having a molecular weight no greater than 60 kD. As defined herein, poly vinyl alcohol (PVA) is not a degradable polymer.

Other aspects of the invention are disclosed infra.

BRIEF DESCRIPTION OF THE DRAWINGS

FIG. 4 shows antitumour activity measured using male SCID mice bearing A2058 human melanoma.

FIG. 5 shows antitumour activity measured using male C57 mice bearing LLC.

DETAILED DESCRIPTION OF THE INVENTION

Figure 1A:
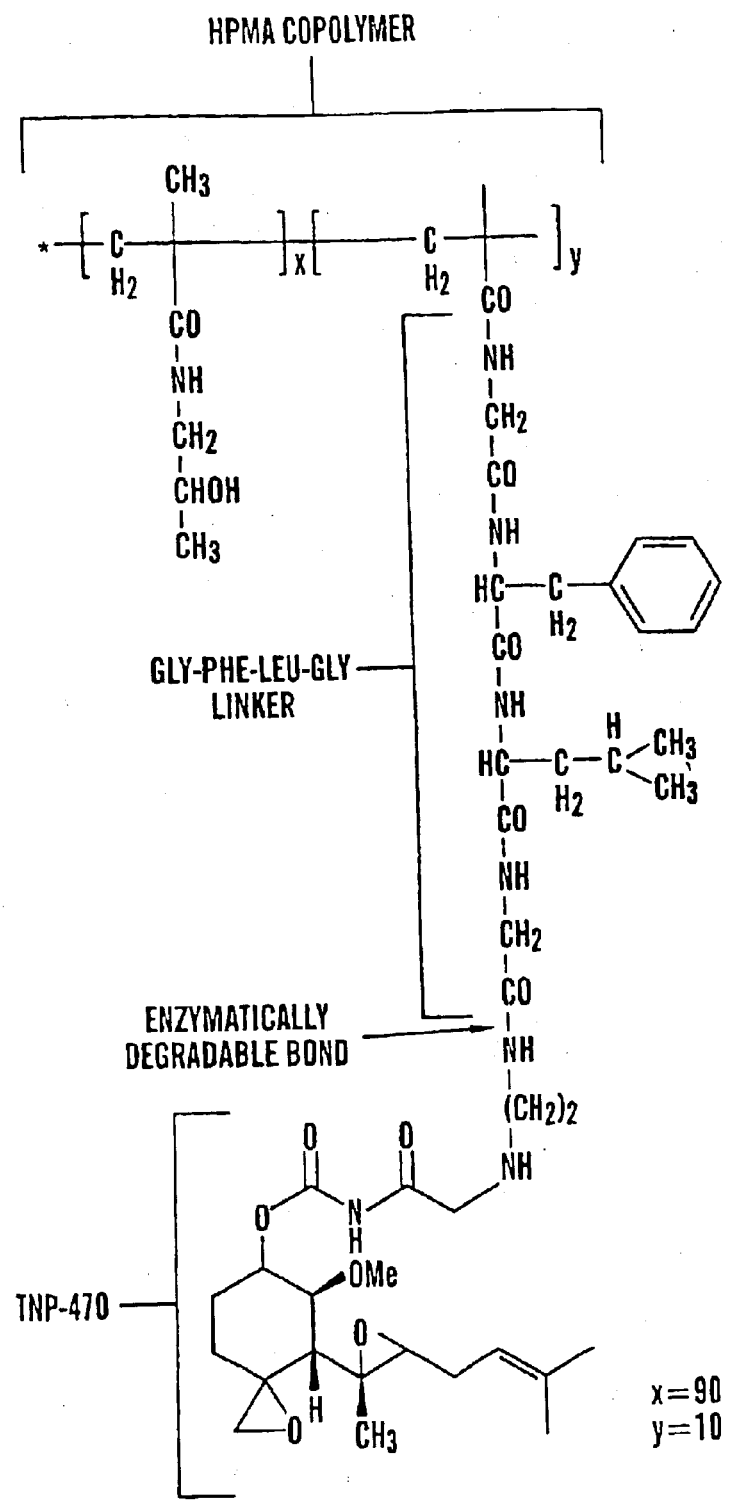
FIG. 1A illustrates the structure of HPMA copolymer-Gly-Phe-Leu-Gly (SEQ ID NO: 1)-ethylenediamine-TNP-470.

The present invention relates to polymer and copolymer conjugates of TNP-470 and TNP-470 species.

In accordance with the present invention, the TNP-470 is linked to a water soluble degradable or non-degradable polymer having a molecular weight in the range of 100 Da to 800 kDa. The components of the polymeric backbone may comprise acrylic polymers, alkene polymers, urethanepolymers, amide polymers, polyimines, polysaccharides and ester polymers. Preferably the polymer is synthetic rather than being a natural polymer or derivative thereof. Preferably the backbone components comprise derivatised polyethyleneglycol and poly(hydroxyalkyl(alk) acrylamide), most preferably amine derivatised polyethyleneglycol or hydroxypropyl(meth)acrylamide-methacrylic acid copolymer or derivative thereof. Dextran/dextrin and polyethylene glycol polymers, or derivatives thereof, may also be used. Preferably, the polymer has a molecular weight no greater than 60 kDa. A most preferred molecular weight range is 15 to 40 kDa.

The TNP-470 and the polymer are conjugated by use of a linker, preferably a cleavable peptide linkage. Most preferably, the peptide linkage is capable of being cleaved by preselected cellular enzymes, for instance, those found in lysosomes of cancerous cells or proliferating endothelial cells. Alternatively, an acid hydrolysable linker could comprise an ester or amide linkage and be for instance, a cis-aconityl linkage. A pH sensitive linker may also be used.

Cleavage of the linker of the conjugate results in release of active TNP-470. Thus the TNP-470 must be conjugated with the polymer in a way that does not alter the activity of the agent. The linker preferably comprises at least one cleavable peptide bond. Preferably the linker is an enzyme cleavable oligopeptide group preferably comprising sufficient amino acid units to allow specific binding and cleavage by a selected cellular enzyme. Preferably the linker is at least two amino acids long, more preferably at least three amino acids long. For example; TNP470 can be conjugated to HPMA copolymer-Gly-Phe-Leu-Gly (SEQ ID NO: 1)-ethylendiamine via nucleophilic attack on the α-carbonyl on the TNP-470 releasing the chlorine to form a compound of formula 1,

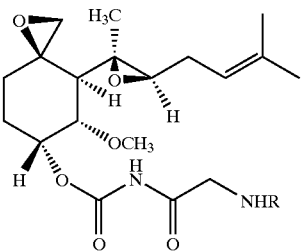

wherein R is $(CH_2)_nR'$, where n is 0 to 3, preferably n is 2, and R' is $NH_2$, O or S. For instance, HPMA copolymer-Gly-Phe-Leu-Gly (SEQ ID NO: 1)-ethylendiamine (100 mg) can be dissolved in DMF (1.0 ml). Then, TNP-470 (100 mg) can be dissolved in 1.0 ml DMF and added to the solution. The mixture is stirred in the dark at 4° C. for 12 h. DMF is then evaporated and the product, HPMA copolymer-TNP-470 conjugate is redissolved in water, dialyzed (10 kDa MWCO) against water to exclude free TNP-470 and other low molecular weight contaminants, lyophilized and stored at −20° C. Reverse phase HPLC analysis using a C18 column, is used to characterize the conjugate. This conjugated structure can be cleaved enzymatically between the glycine residue of the peptide and the ethylenediamine residue (See FIG. 1A).

The resultant product is 6-O-(N-ethylaminoglycinylcarbmoyl) fumagillol, which has the structure shown below.

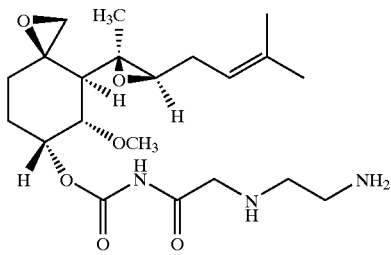

This is the compound of formula 1, where R is $—(CH_2)_2NH_2$. This compound has a bis-epoxide functionality. Accordingly, it will also have anti-tumor activity, particularly antiangiogenic activity. This compound, or its' pharmaceutically acceptable salt, should be able to be cleaved, like TNP-470, to the active metabolite set forth below (2).

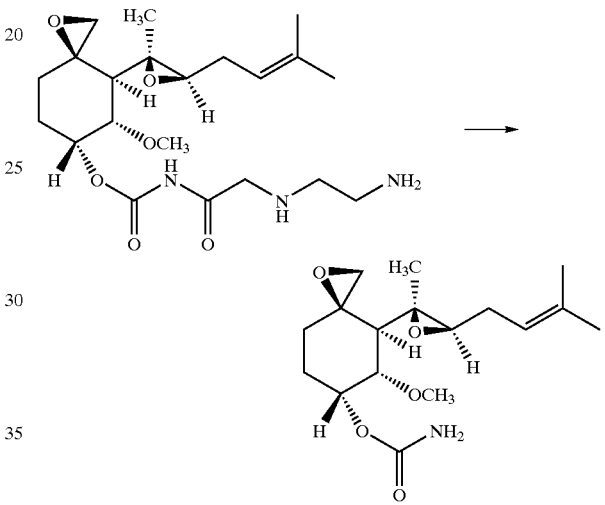

(2)

This should be water soluble. This product can be used by itself without the conjugate. The compound can be modified by known means and should still retain its water soluble, as well as its antiangiogenic, properties. These modifications can be made by known means, such as those used with other fumagillian derivatives. Preferably nucleophiles of the formula $(NH_2)_n$ R, wherein n is 1 to 2 and R is H, O or S can be used to substitute for the Cl of TNP-470.

One mode for synthesis of the compound of formula 1, where R is $—(CH_2)_2NH_2$ is illustrated below.

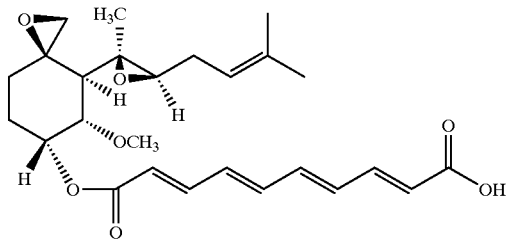

Fumagillin
Mol. Wt. 458.55
$C_{26}H_{34}O_7$

J.K. Landquist
J. Chem. Soc. 4237 (1956)
0.1 N NaOH/N$_2$/4° C.
4 hr. (extract with Et$_2$O)

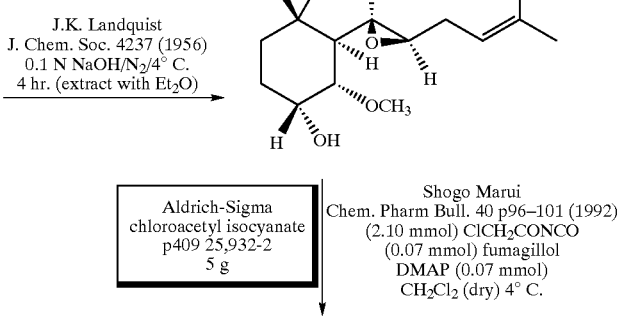

Aldrich-Sigma
chloroacetyl isocyanate
p409 25,932-2
5 g

Shogo Marui
Chem. Pharm Bull. 40 p96–101 (1992)
(2.10 mmol) ClCH$_2$CONCO
(0.07 mmol) fumagillol
DMAP (0.07 mmol)
CH$_2$Cl$_2$ (dry) 4° C.

-continued

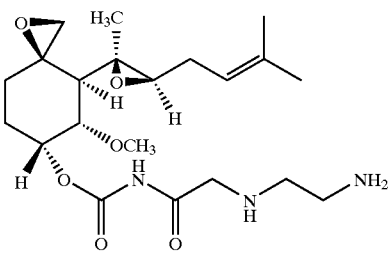 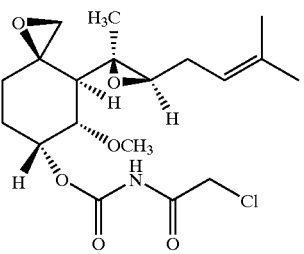

Satchi-Feinaro
Nature Medicine 2004
NH₂CH₂CH₂NH₂
────────────────→
DMF/4° C.

Aldrich-Sigma
p853
39, 108-5
100 ml

TNP-470

Also included within the scope of the present invention are compositions that comprise, as an active ingredient, the organic and inorganic addition salts of the above-described compound and combinations thereof; optionally, in association with a conjugate, diluent, slow release matrix, or coating.

The organic or inorganic addition salts of the water soluble antiangiogenic compounds and conjugates thereof contemplated to be within the scope of the present invention include salts of such organic moieties as acetate, trifluoroacetate, oxalate, valerate, oleate, laurate, benzoate, lactate, tosylate, citrate, maleate, fumarate, succinate, tartrate, naphthalate, and the like; and such inorganic moieties as Group I (i.e., alkali metal salts), Group II (i.e. alkaline earth metal salts) ammonium and protamine salts, zinc, iron, and the like with counterions such as chloride, bromide, sulfate, phosphate and the like, as well as the organic moieties referred to above.

Pharmaceutically acceptable salts are preferred when administration to human subjects is contemplated. Such salts include the non-toxic alkali metal, alkaline earth metal and ammonium salts commonly used in the pharmaceutical industry including sodium, potassium, lithium, calcium, magnesium, barium, ammonium and protamine salts which are prepared by methods well known in the art. The term also includes non-toxic acid addition salts which are generally prepared by reacting the compounds of this invention with a suitable organic or inorganic acid. Representative salts include hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napthylate and the like.

Preferred polymers for use with the present invention are HPMA copolymers with methacrylic acid with pendent oligopeptide groups joined via peptide bonds to the methacrylic acid with activated carboxylic terminal groups such as paranitrophenyl derivatives or ethylene diamine.

In a preferred embodiment the polymeric backbone comprises a hydroxyalkyl(alk)acrylamide methacrylamide copolymer, most preferably a copolymer of hydroxypropyl (meth)acrylamide copolymer (HPMA). The HPMA prior to attachment of the TNP-470 has the structure set forth below:

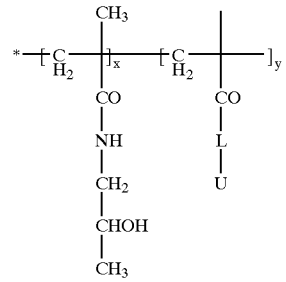

y can be in the range of 0.01–100 and x can be in the range 0–99.99. y is preferably in the range of 0.04–20 and x is preferably in the range 80–99.96. Preferably L is an oligopeptide group containing between 2 and 10 peptide moieties, most preferably 3 or 4.

In a most preferred embodiment, L is a Gly-Phe-Leu-Gly- (SEQ ID NO: 1) linkage. In one embodiment, U is an ONp group, wherein Np is a p-nitrophenyl group. Preferably y is in the range 0.3 to 15 and x is in the range of 99.7 to 85. Most preferably, y is in the range of 5–10 and x is in the range of 90–95. In a more preferred embodiment, the polymeric backbone is HPMA copolymer-Gly-Phe-Leu-Gly (SEQ ID NO: 1)-ethylenediamine having the values for x and y as defined above.

In a most preferred embodiment of HPMA copolymer TNP-470 conjugate has the structure set forth in FIG. 1A.

HPMA polymers and use thereof are disclosed in WO 01/36002.

In another embodiment, the conjugate is a liposome/TNP-470 conjugate. Preferably, the conjugate is a pegylated liposomal TNP-470. An exemplary conjugate comprises:
a) TNP-470;
b) N-(carbonyl-methoxypolyethylene glycol 2000)-1,2-distearoyl-sn-glycero-3-phosphoethanolamine sodium salt;
c) fully hydrogenated soy phosphatidylcholine;
d) cholesterol;

Histidine, hydrochloric acid and/or sodium hydroxide, ammonium sulfate, and sucrose; wherein the weight percentage ratio of a:b:c:d is about 1.0:1.60:4.80:1.60 mg/mL respectively.

While the antiangiogenic agent conjugate and/or water soluble antiangiogenic compound may rely for its localization at a solid tumor, or other sites of active angiogenesis, primarily upon EPR, it may be desirable to attach ligands allowing active targeting. A preferred targeting ligand is directed to the integrin a Vβ3 and contains the tripeptide sequence RGD or RGD4C (cyclic RGD). Antibodies or ligands directed to cell receptors or other upregulated molecules present on the cell surface may also be used. See, e.g. 28.

The conjugate and the water soluble antiangiogenic compound of the present invention is useful in inhibiting the angiogenic function of endothelial cells both in vitro and in vivo. Of particular interest is the prevention or inhibition of endothelial cell differentiation into capillary structures. The endothelial cells amenable to inhibition by the conjugate are present at several sites in a mammal and include but are not limited to dermis, epidermis, endometrium, retina, surgical sites, gastrointestinal tract, liver, kidney, reproductive system, skin, bone, muscle, endocrine system, brain, lymphoid system, central nervous system, respiratory system, umbilical cord, breast tissue, urinary tract and the like. The method of treatment of the present invention using the conjugate and compound is particularly useful in preventing or inhibiting angiogenesis by endothelial cells at sites of inflammation and tumorigenesis.

The conjugate and compound is particularly useful in methods of inhibiting angiogenesis at a site of tumorigenesis in a mammal. The conjugate and compound administered at such sites prevents or inhibits blood vessel formation at the site thereby inhibiting the development and growth of the tumor. Tumors which may be prevented or inhibited by preventing or inhibiting angiogenesis with the conjugate include but are not limited to melanoma, metastases, adenocarcinoma, sarcomas, thymoma, lymphoma, lung tumors, liver tumors, colon tumors, kidney tumors, non-Hodgkins lymphoma, Hodgkins lymphoma, leukemias, uterine tumors, breast tumors, prostate tumors, renal tumors, ovarian tumors, pancreatic tumors, brain tumors, testicular tumors, bone tumors, muscle tumors, tumors of the placenta, gastric tumors and the like.

In providing a mammal with the conjugate and/or compound, preferably a human, the dosage of administered conjugate will vary depending upon such factors as the mammal's age, weight, height, sex, general medical condition, previous medical history, disease progression, tumor burden, route of administration, formulation and the like. For example, a suitable dose of the conjugate or compound for a mammal in need of treatment as described herein is in the range of about 1 mg to about 2000 mg TNP-470 per kilogram of body weight.

The route of administration may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like.

The present invention encompasses combination therapy in which the conjugate or compound is used in combination with a chemotherapeutic agent such as Taxol, cyclophosphamide, cisplatin, gancyclovir and the like. The chemotherapeutic agent may also be conjugated to a polymer. Such a therapy is particularly useful in situations in which the mammal to be treated has a large preexisting tumor mass which is well vascularized. The chemotherapeutic agent serves to reduce the tumor mass and the conjugate prevents or inhibits neovascularization within or surrounding the tumor mass. The chemotherapeutic agent may also be administered at lower doses than normally used and at such doses may act as an antiangiogenic agent.

The present invention is further illustrated by the following Examples. These examples are provided to aid in the understanding of the invention and are not construed as a limitation thereof.

EXAMPLE 1

Methods

Materials

A random copolymer of HPMA copolymerized with methacryloyl-Gly-Phe-Leu-Gly (SEQ ID NO: 1)-p-nitrophenyl ester (HPMA copolymer-MA-GFLG (SEQ ID NO: 1)-ONp) incorporating approximately 10 mol % of the MA-GFLG (SEQ ID NO: 1)-ONp monomer units was prepared as previously reported [24] provided by Polymer Laboratories (UK). The polymeric precursor was used for ethylenediamine (en) incorporation and the product HPMA copolymer-GFLG (SEQ ID NO: 1)-en had a Mw of 31,600 Da and polydispersity (PD) of 1.66. TNP-470 was kindly provided by Douglas Figg from the NCI (USA). 2-Propanol, methanol, orthophosphoric acid and chloroform were from Sigma (all HPLC grade). Dimethylformamide (DMF) and dimethylsulfoxide (DMSO) were from Aldrich (USA). All other chemicals were of analytical grade from Aldrich (USA) and Fisher Chemicals (USA) unless otherwise stated. Vivacell 70 ml (10 kDa MW cut-off PES) was from Viva-Science (USA). Isoflurane was purchased from Baxter Healthcare Corporation (USA). Matrigel basement membrane matrix (from Engeibreth-Hoim-Swarm mouse tumor) was purchased from Becton Dickinson (USA). Avertin was purchased from Fisher (USA).

A2058 human melanoma cells were from the ATCC. LLC cells were passaged from mouse to mouse as previously described[47]. Cells were maintained in DMEM medium containing 10% inactivated fetal bovine serum (Life Technologies, Inc.), 0.29 mg/ml L-glutamine, 100 units/ml penicillin and 100 µg/ml streptomycin (GPS) (Gibco) in a humidified 5% $CO_2$ incubator at 37° C. BCE cells were isolated in our laboratory, and cultured in a humidified 10% $CO_2$ incubator at 37° C. as described[48]. BCE cells were grown in DMEM medium supplemented with 10% bovine calf serum (BCS), GPS, and 3 ng/ml basic fibroblast growth factor (bFGF). C57BL/6J mice were purchased from Jackson Laboratories (USA), SCID mice were from Massachusetts General Hospital (USA) and BALB/c mice were from Charles River (USA).

Synthesis

TNP-470 was conjugated to HPMA copolymer-Gly-Phe-Leu-Gly (SEQ ID NO: 1)-ethylendiamine via nucleophilic attack on the α-carbonyl on the TNP470 releasing the chlorine. HPMA copolymer-Gly-Phe-Leu-Gly (SEQ ID NO: 1)-ethylendiamine (100 mg) was dissolved in DMF (1.0 ml). Then, TNP-470 (100 mg) was dissolved in 1.0 ml DMF and added to the solution. The mixture was stirred in the dark at 4° C. for 12 h. DMF was evaporated and the product, HPMA copolymer-TNP-470 conjugate was redissolved in water, dialyzed (10 kDa MWCO) against water to exclude free TNP-470 and other low molecular weight contaminants, lyophilized and stored at −20° C. Reverse phase HPLC analysis using a C18 column, was used to characterize the conjugate.

Bovine Capillary Endothelial (BCE) Cell Proliferation Assay

BCE cells were obtained and grown as previously described[48]. For the proliferation assay, cells were washed with PBS and dispersed in a 0.05% trypsin solution. Cells were suspended (15,000 cells/ml) in DMEM supplemented with 10% BCS and 1% GPS, plated onto gelatinized 24-well culture plates (0.5 ml/well), and incubated for 24 h (37° C., 10% $CO_2$). The media was replaced with 0.25 ml of DMEM, 5% BCS and 1% GPS and the test sample applied. Cells were challenged with free or conjugated TNP-470 (10 pg/ml to 1 µg/ml TNP-470-equivalent concentration). After 30 min of incubation, media and bFGF were added to obtain a final volume of 0.5 ml of DMEM, 5% BCS, 1% GPS and 1 ng/ml bFGF. Control cells were grown with or without bFGF. After 72 hr, cells were dispersed in trypsin, resuspended in Hematall (Fisher Scientific, Pittsburgh, Pa.), and counted in a Coulter counter.

Chick Aortic Ring Assay:

Aortic arches were dissected from day-14 chick embryos, cut into cross-sectional fragments, and implanted in vitro in Matrigel using a modification of methods previously described (V. Muthukkaruppan, personal communication). When cultured in MCDB-131 medium supplemented with 5% fetal bovine serum, endothelial cells sprouted and vascular channel formation occurred within 24–48 hours. Free or conjugated TNP-470 (10 pg/ml to 1 µg/ml) was added to the culture.

Hepatectomy Model

Male C57BL/6J mice underwent a partial hepatectomy through a midline incision after general anesthesia with isoflourane[33]. Free or conjugated TNP-470 (30 mg/kg) were given s.c. every other day for 8 days beginning on the day of surgery according to the scheme described in FIG. 4a. Alternatively, the doses given were 60 mg/kg the day of surgery and 4 days later or 120 mg/kg once on the day of the partial hepatectomy. The liver was harvested on the $8^{th}$ day, weighed and analyzed by histology.

Evaluation of the Body Distribution of Free TNP-470 and HPMA Copolymer-TNP-470 in Mice Bearing s.c. LLC Male C57BL/6J mice were inoculated with $5 \times 10^6$ viable LLC cells s.c. and the tumor was allowed to grow to a volume of approximately 100 mm$^3$. Animals were injected i.v. with free or conjugated TNP-470 (30 mg/kg). Intracerebral withdrawal of CSF from the brain of C57BL/6J mice was performed using a Model 310 stereotaxic apparatus (Stoelting Co., Wooddale Ill.) according to stereotaxic coordinates described in the mouse brain atlas[49] and the method described in Waynforth[50]. Once the desired amount of fluid was obtained (approximately 20 µl), the animal was euthanized via cervical dislocation at times up to 72 h. Tumors, major organs, blood, urine and CSF were collected and homogenized. Then a TNP-470 species (sometimes referred to herein as TNP-470) was extracted in chloroform. Following evaporation of the chloroform, samples were redissolved and high-performance liquid chromatography (HPLC)/tandem Mass Spectrometry (LC-MS/MS) was used to determine the amount of free TNP-470 in the samples as previously described[36].

Evaluation of Antitumor Activity of HPMA Copolymer-TNP-470

Male C57BL/6J mice (~8 weeks, ~20 g) were inoculated with $5 \times 10^6$ viable LLC or A2058 melanoma cells s.c. The tumors were allowed to grow to a volume of approximately 100 mm$^3$. Animals were injected i.v. with free TNP-470 or HPMA copolymer-TNP-470 (30 mg/Kg TNP-equiv.) or saline (250 µl i.v.). Each group consisted of 5 mice. Mice were euthanized when tumors reached or surpassed a size equivalent to 30% of their body weight. Animals were weighed daily and observed for signs of tumor progression and euthanized if their body weight decreased below 80% of their starting weight. Animals were monitored for general health, weight loss, and tumor progression. At termination, mice underwent post-mortem examination and tumors were dissected and weighed. A similar experiment was repeated in which treatment with escalating doses of the conjugate was initiated when tumors reached. 500 mm$^3$. The same dosing schedule was repeated with white SCID male mice (~8 weeks, 20 g) inoculated with $5 \times 10^6$ viable A2058 human melanoma cells s.c. and treated as described above.

Statistical Methods

All of the in vitro data are expressed as the mean±standard deviation of the mean (S.D.). All of the in vivo data are expressed as the mean±standard error of the mean (S.E.). Statistical significance was assessed using the Student's t-test. P values of 0.05 or less were considered statistically significant.

Results

Synthesis and Characterization

Figure 1B:
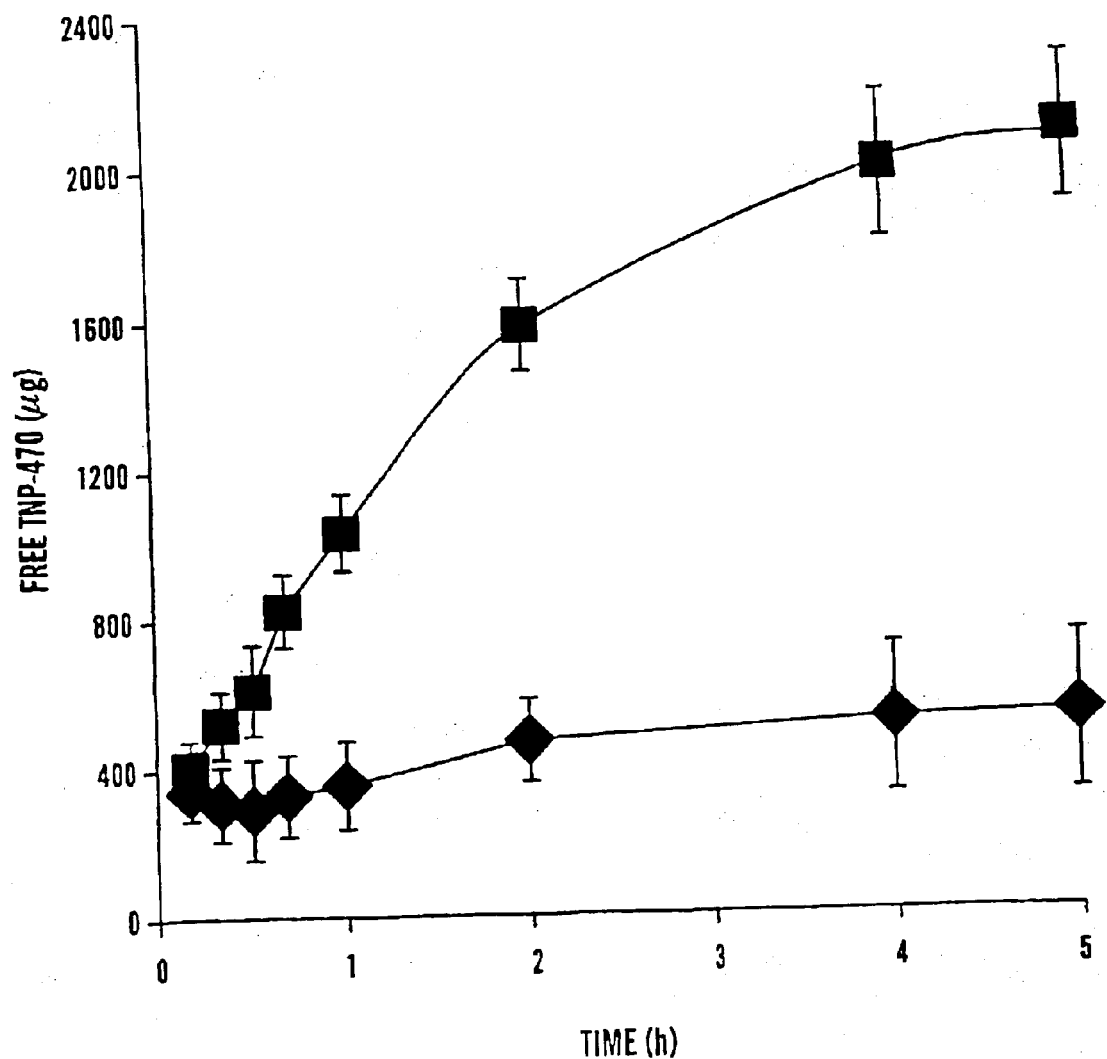
FIG. 1B shows in vitro release of TNP-470 from HPMA copolymer in the presence (-■-) and absence ((-♦-) of cathepsin B.

HPMA copolymer-Gly-Phe-Leu-Gly (SEQ ID NO: 1)-ethylenediamine-TNP-470 conjugate (FIG. 1A) was synthesized, purified and characterized by HPLC. Gly-Phe-Leu-Gly (SEQ ID NO: 1) polymer-TNP-470 linker was designed to permit intralysosomal TNP470 liberation due to action of the lysosomal cysteine proteases[29], such as cathepsin B. It has been shown that cathepsin B is overexpressed in many tumor cells[30]. The conjugate accumulates selectively in the tumor tissue due to the EPR effect and is slowly internalized into endothelial cells in the tumor bed by fluid-phase pinocytosis. The conjugate should not internalize into normal quiescent endothelial cells, hence will not be exposed to lysosomal enzymes leaving the linker intact. Free TNP-470 eluted as a single peak with a retention time of 13.0 mm while the conjugate eluted as a wider peak at 10.0 mm (results not shown). Free drug was negligible (<0.01% of total TNP-470) following repeated purification by dialysis. TNP-470 is not water-soluble but became soluble following conjugation with HPMA copolymer. The conjugate was stable for three days in phosphate buffered saline or citrate buffer, pH 5.5, 0.2 M at 37° C. However, under the same conditions with the addition of the lysosomal enzyme cathepsin B, the linker between the polymer and the drug (Gly-Phe-Leu-Gly[31]) (SEQ ID NO: 1) was cleaved and TNP-470 was released (FIG. 1B). These conditions imitate the lysosomal environment in endothelial cells where lysosomal enzymes, such as cathepsin B, are present. TNP-470 release from the conjugate reached a plateau within 5 h of incubation with cathepsin B and did not increase appreciably even after 5 days. The incubated solution was then analyzed and had a TNP-470 content of approximately 10 mol %. We next tested the HPMA copolymer-TNP-470 conjugate activity in two in vitro angiogenesis assays: the endothelial cell proliferation and the chick aortic ring assays.

Bovine Capillary Endothelial (BCE) Cell Proliferation

Figure 2A:
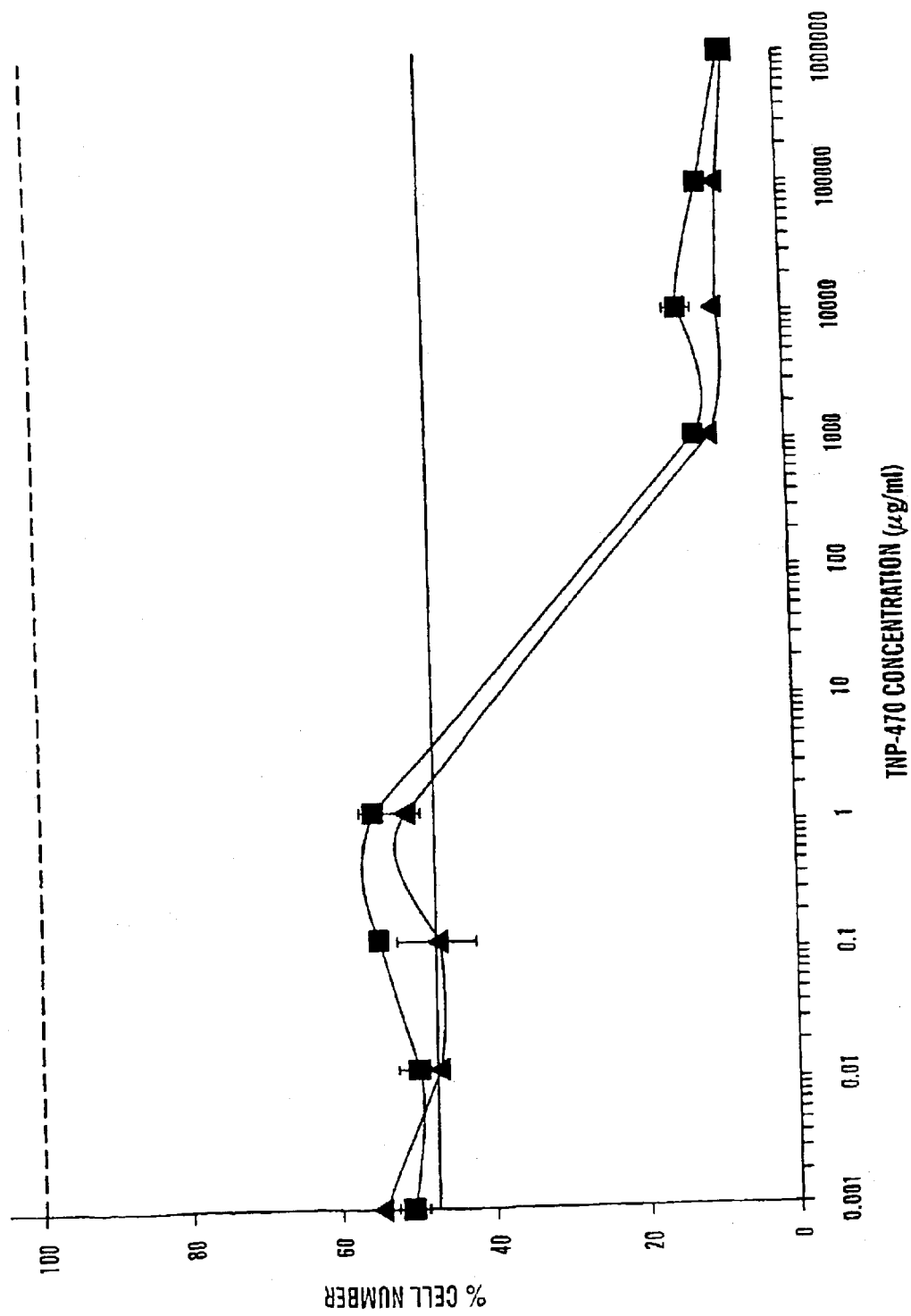
FIG. 2A shows inhibition of BCE proliferation in vitro after 72 h. TNP470 (-▲-) and HPMA copolymer-Gly-Phe-Leu-Gly (SEQ ID NO: 1)-en-TNP-470 (-■-) had similar cytostatic effect on bFGF-induced proliferation of endothelial cells at doses lower than 1 μg/ml and cytotoxic effect at doses higher than 1 μg/ml. The dotted line represents the proliferation of bFGF-induced BCE cells ( - - - ) and the solid line represents the BCE cell proliferation in the absence of bFGF (-).

To determine if HPMA copolymer-TNP-470 was active in endothelial cells we tested its inhibitory effect on BCE cell proliferation in vitro. BCE cell growth, stimulated by bFGF, was inhibited similarly by TNP-470 and HPMA copolymer-TNP-470 (FIG. 2A). Both free and conjugated TNP-470 inhibited bFGF-induced proliferation. (cytostatic effect) of BCE cells from 10 pg/ml to 1 µg/ml TNP-470-equivalent concentration. However, at doses higher than 1 µg/ml both free and conjugated TNP-470 were cytotoxic. These data are in agreement with published results of free TNP-470 on different endothelial cells[11,32].

Chick Aortic Ring Assay

Figure 2B:
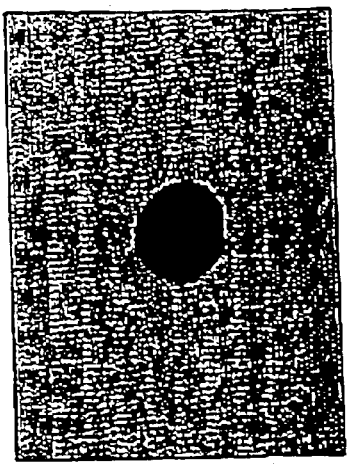
FIG. 2B shows the chick aortic ring endothelial sprouting assay. The effect of TNP-470 (central panel) and HPMA copolymer-Gly-Phe-Leu-Gly (SEQ ID NO: 1)-en-TNP-470 (right panel) at 100 pg/ml TNP-470 equivalent-dose are shown; and a control chick aortic ring (left panel) with abundant sprouting.
Figure 2B:
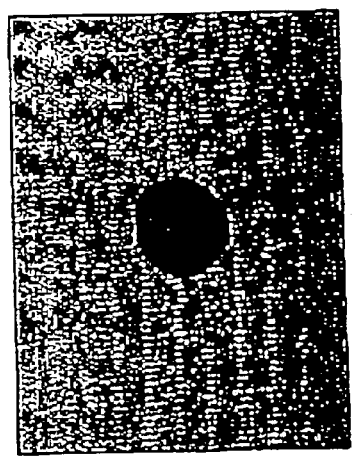
Figure 2B:
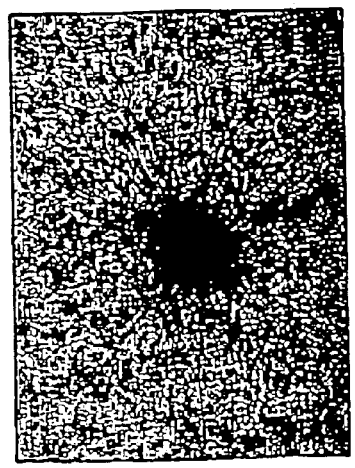

Having demonstrated that the conjugate inhibited in vitro endothelial cell growth, an ex-vivo model of chick aortic rings implanted in Matrigel was utilized to further characterize the HPMA copolymer-TNP-470 conjugate. Both free and conjugated TNP-470 reduced the number and length of vascular sprouts growing from the chick aortic ring at 50 pg/ml and completely prevented outgrowth at 100 pg/ml (FIG. 2B). A control aortic ring (left panel) showed abundant sprouting. Similar dose dependency was found for free TNP-470 in a mouse aortic ring assay (Moulton, unpublished results).

Hepatectomy

We have shown that HPMA copolymer-TNP-470 was equally-active as the free TNP-470 in vitro. Therefore, we evaluated its antiangiogenic activity in vivo.

Figure 3A:
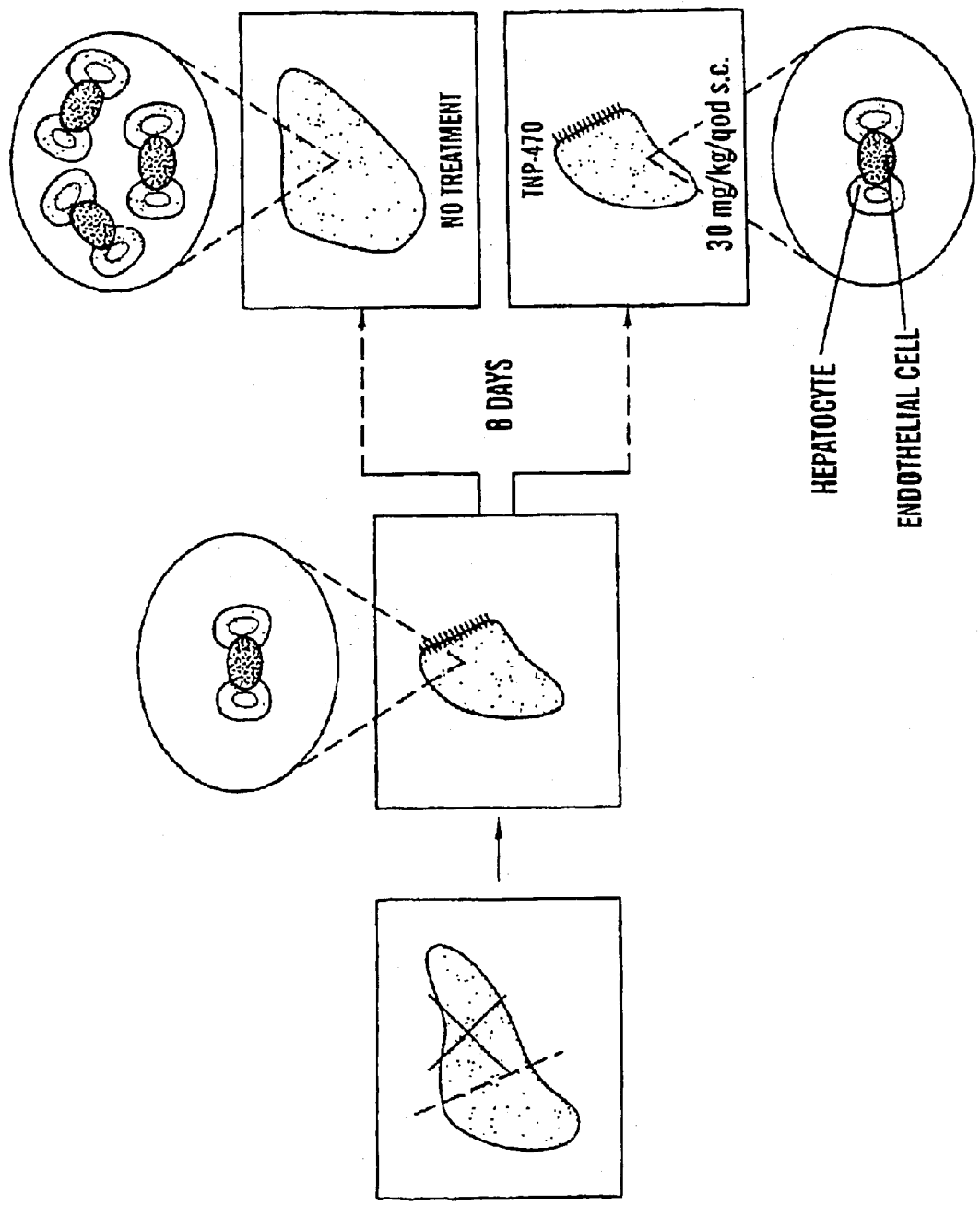
FIG. 3A shows a schematic representation of the hepatectomy model. Untreated livers regenerate in 8 days, but they do not regenerate when treated with TNP-470 30 mg/kg/q.o.d s.c.
Figure 3B:
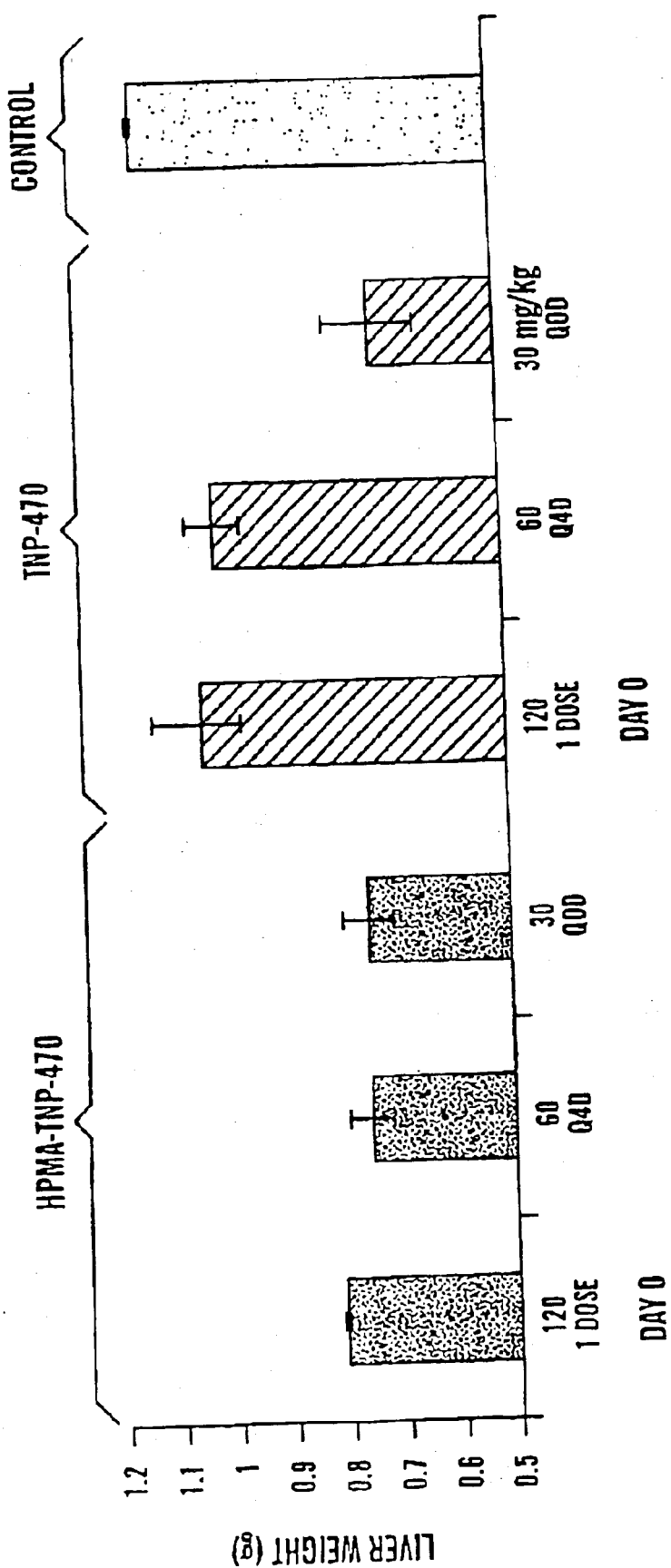
FIG. 3B shows that free TNP-470 (stripes columns) inhibited liver regeneration when used at 30 mg/kg/q.o.d s.c. However, it did not inhibit liver regeneration at other dosing schedules. Conjugated TNP-470 (solid columns) inhibited liver regeneration at 30 mg/kg/q.o.d s.c. or 60 mg/kg/q.2.d s.c. or even at a single dose of 120 mg/kg/day of operation s.c. compared to the control regenerated group (dotted columns).

Before testing the conjugate in tumor models in vivo, we established the efficacy of HPMA copolymer-TNP-470 conjugate in the hepatectomy model (FIG. 3A). This nonneoplastic model is a relatively fast (8 days) in vivo angiogenesis-dependent process[33]. We employed the hepatectomy model to compare the endothelial cell inhibitory activity of free and conjugated TNP-470, because liver regeneration post hepatectomy is angiogenesis-dependent, similar to tumor growth[33,34]. Following partial hepatectomy, control mice regenerated their resected liver to their pre-operative mass (~1.2 g) by post-operative day 8 (FIG. 3B). In mice treated subcutaneously (s.c.) with free TNP-470 or its polymer-conjugated form at 30 mg/kg every other day (q.o.d), the regeneration of the liver was inhibited and livers reached the average size of 0.7 g on post-operative day 8 (FIG. 3B). Free TNP-470 did not inhibit liver regeneration when injected at 60 mg/kg every four days or at a single injection of 120 mg/kg at the day of the hepatectomy. However, HPMA copolymer-TNP-470 conjugate had an equivalent effect as the 30 mg/kg q.o.d. dosing schedule when given every 4 days (q.4.d.) at 60 mg/kg or at a single dose of 120 mg/kg on the day of hepatectomy. This suggests that the conjugate has a longer circulation time than the free TNP-470 in vivo and/or that the conjugate accumulates at the site of proliferating endothelial cells, leading to sustained release of TNP-470 from the polymer. Because liver regeneration is regulated by endothelial cells[33,34], it was expected that a similar effect would occur with proliferating endothelial cells in tumor tissue, where the conjugate accumulates due to the EPR effect.

Early Mouse Development

Figure 3C:
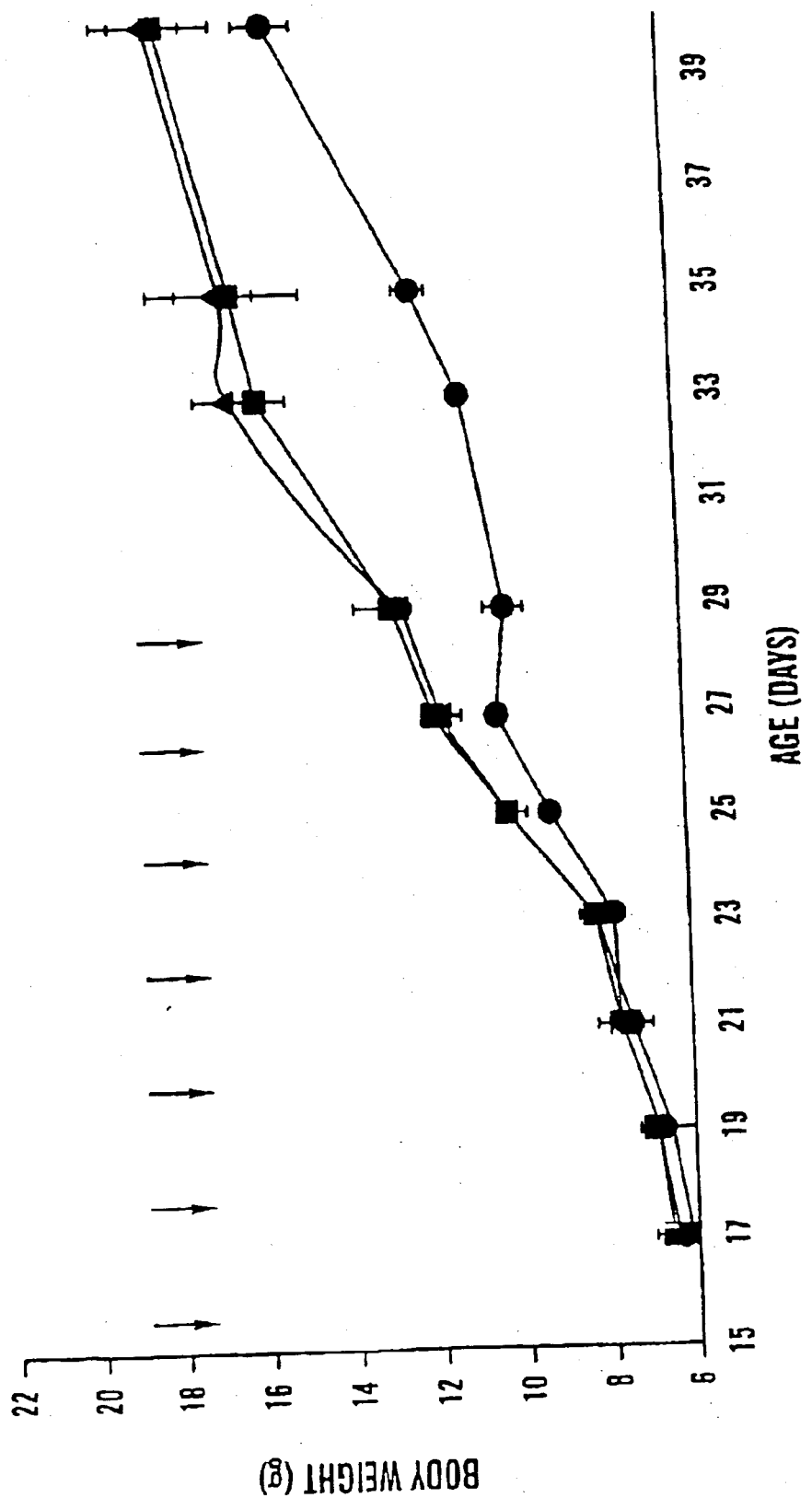
FIG. 3C shows that free TNP-470 (-●-) causes delay in newborn mice development, but did not affect body weight when used in the conjugated form (-▲-) similar to the control mice (-■-). Arrows represent days of treatment. Data represent mean±SE, n=9 mice per group.

Free and conjugated TNP-470 were injected into 7 and 17 day-old BALB/c mice in order to test their effects on normal development. Free TNP-470 inhibited growth, by inhibiting weight gain at this critical age. However, HPMA copolymer-TNP-470 conjugate-treated mice developed similarly to the control group injected with saline (FIG. 3C). These results differed from the results obtained from the hepatectomy experiments. HPMA copolymer-TNP-470 conjugate inhibited liver regeneration following hepatectomy but did not inhibit normal development in the newborn mice. A possible explanation is that the conjugate extravasated through leaky vessels in the liver following surgery (i.e., same inhibition as seen in wound healing delayed by TNP-470 [35]). However, the conjugate did not leak from normal vessels developing in the newborn.

Figure 4A:
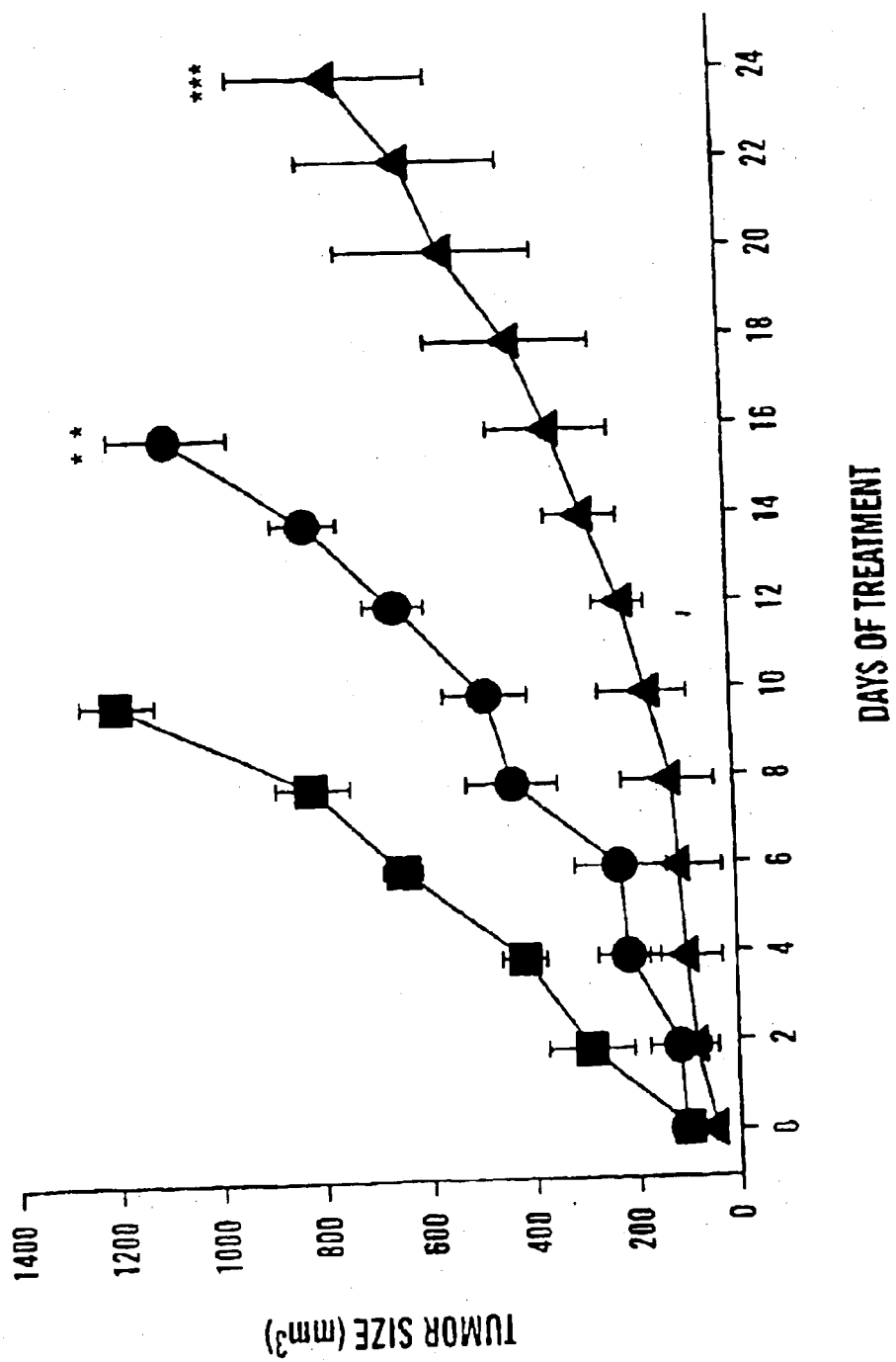
FIG. 4A shows the effect of TNP-470 (-●-); HPMA copolymer-Gly-Phe-Leu-Gly (SEQ ID NO: 1)-en-TNP-470 (-▲-); and control mice (-■-) on tumors. Data represent mean±SE, n=8 mice per group. P values of <0.05 were marked as *, P<0.03 , P<0.01 *.
Figure 4B:
FIG. 4B shows SCID mice and excised tumors correlating to panel (A) at day 8 of treatment.
Figure 4C:
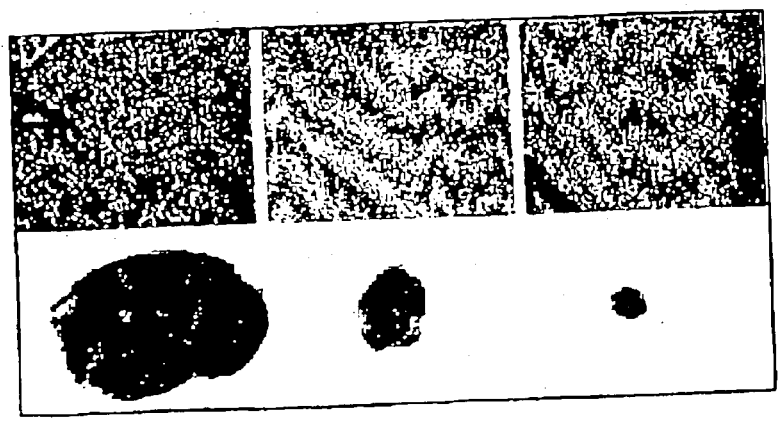
FIG. 4C shows H & E staining of tumors excised from animals in different groups on day 8 at high and low power.

Evaluation of Antitumor Activity of HPMA Copolymer-TNP-470 on SCID Mice Bearing s.c. A2058 Human Melanoma Mice bearing s.c. A2058 melanoma showed increased survival when treated with free and conjugated TNP-470 (T/C=0.34 for TNP-470 and 0.12 for the conjugate) (FIG. 4A). T/C was defined as the ratio of the mean volume of tumor of the treated animals (T) divided by the mean volume of tumor of the untreated control group (C). During this study there were neither deaths due to toxicity nor weight loss in the mice treated with the conjugate, indicating dose escalation of the conjugate to be possible. A significant decrease in tumor growth rate was observed in animals treated with TNP-470 (P<0.03) and with HPMA copolymer-TNP-470 (P<0.05) compared to controls (FIG. 4A, B, C). FIG. 4C presents histological sections of tumors representing the three treated groups (saline, free or conjugated TNP-470) stained with H & E and showing viable tumor cells in all.

Figure 5A:
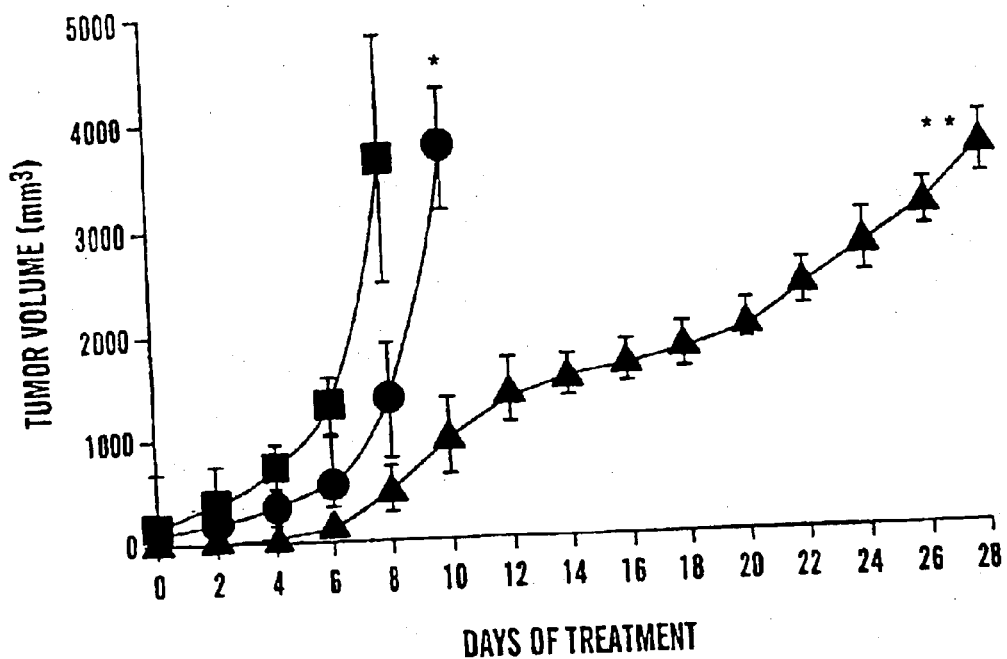
FIG. 5A shows the effect of TNP-470 at 30 mg/kg/q.o.d. s.c. (-●-); HPMA copolymer-Gly-Phe-Leu-Gly (SEQ ID NO: 1)-en-TNP-470 at 30 mg/kg/q.o.d. s.c. (-▲-) on tumor growth; control mice (-■-) are also shown. Data represent mean±SE, n=10 mice per group.
Figure 5B:
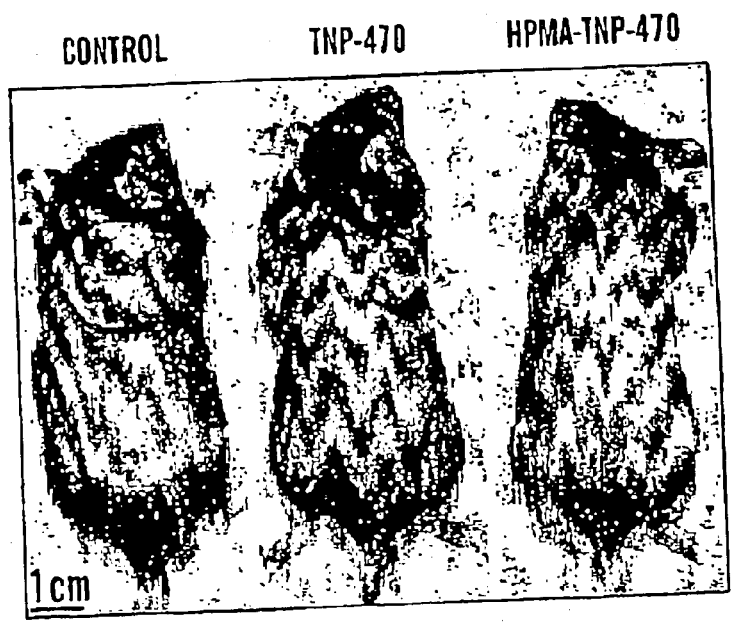
FIG. 5B shows representative C57 mice correlating to (A) on day 10 following treatment.
Figure 5C:
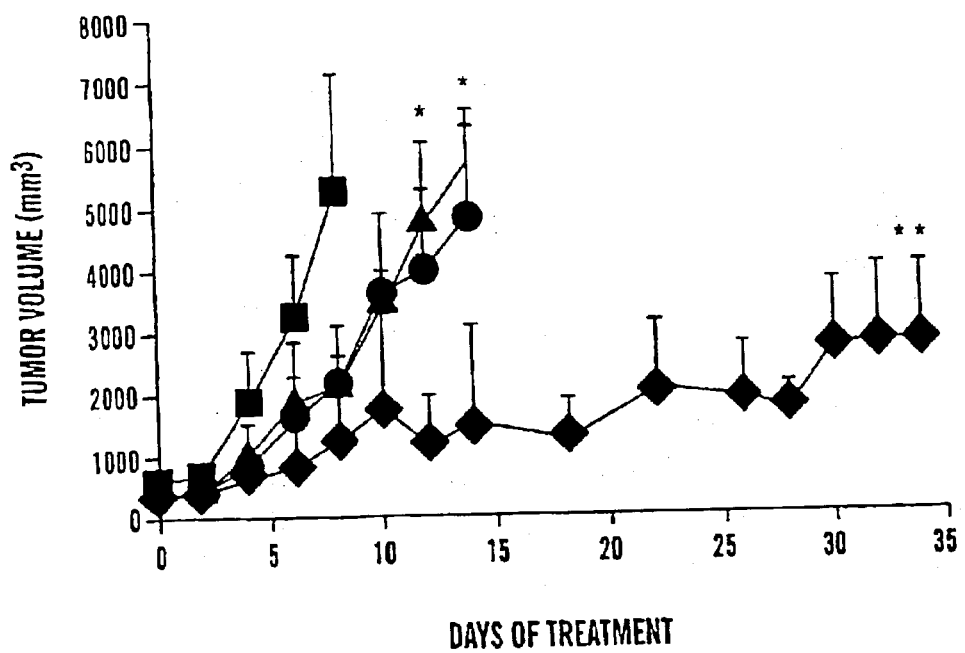
FIG. 5C shows dose escalation of EPMA copolymer-Gly-Phe-Leu-Gly (SEQ ID NO: 1)-en-TNP-470: at 30 (-▲-), at 60 (-●-) and at 90 mg/kg/q.o.d. (-♦-) and control mice (-■-) are shown. Data are mean±SE, n=10 mice per group.
Figure 5D:
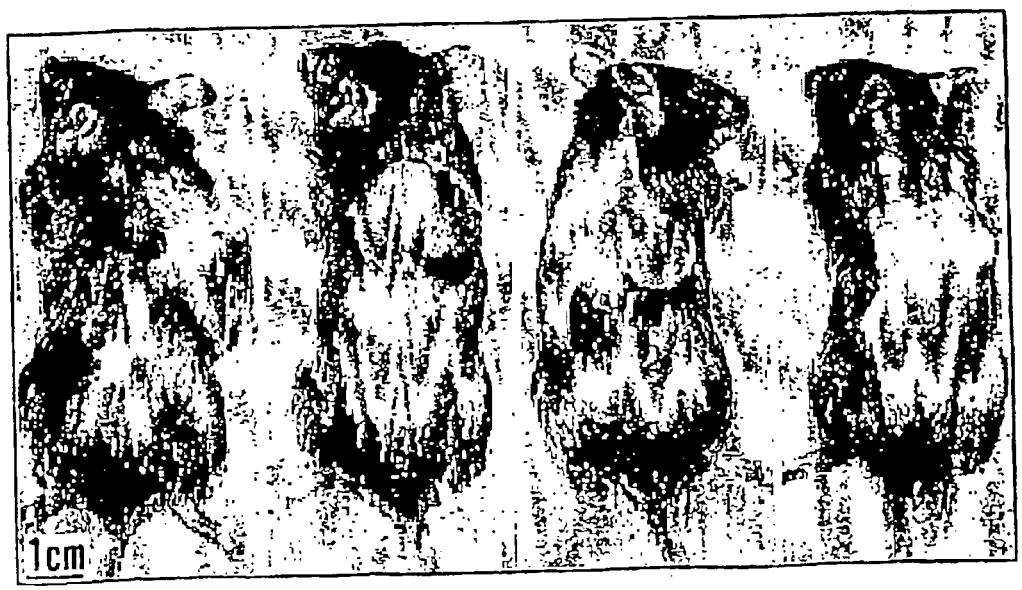
FIG. 5D shows C57 mice correlaing to (C). P values of <0.05 were marked as *, P<0.03 as , P<0.01 as *.

Evaluation of Antitumor Activity of HPMA Copolymer-TNP-470 on C57BL/6J Mice Bearing s.c. LLC Mice bearing s.c. LLC showed increased survival when treated with free and bound TNP-470 at equivalent concentration of TNP-470 of 30 mg/kg q.o.d. HPMA copolymer-TNP-470 exhibited superior antitumor activity compared to free TNP-470. On day 8, when control mice were sacrificed, HPMA copolymer-TNP-470 inhibited tumor growth by 86% (P<0.03) whereas free TNP-470 by 67% (P<0.05) (FIG. 5A, B). In addition, the conjugate did not induce weight loss whereas free TNP-470 did (data not shown). Since HPMA copolymer-TNP-470 did not induce weight loss, we tested the conjugate in LLC-bearing mice at the higher doses of 60 and 90 as well as 30 mg/kg/q.o.d. The conjugate inhibited tumor growth equally at 30 or 60 mg/kg/q.o.d (P<0.03, T/C=0.4, day 8). Tumor suppression was significantly enhanced at 90 mg/kg/q.o.d (P<0.05, T/C=0.24, day 8) (FIG. 5C, D). Even at the higher dose of 90 mg/kg/q.o.d., there was no animal weight loss, indicating we did not reach the maximum tolerated dose (MTD). Free TNP-470 at these doses is known to be toxic to the mice. In this set of experiments treatment was started when tumors reached 500 mm³, therefore results differed from previous experiments where treatment started when tumors were 100 mm³.

Evaluation of TNP-470 and HPMA Copolymer-TNP-470 in the Cerebrospinal Fluid of Mice Bearing s.c. LLC HPLC-Mass spectrometry (LC-MS/MS) showed that free TNP-470 is present in the cerebrospinal fluid (CSF) of mice with s.c. LLC tumor following i.v. administration of the drug. However, when HPMA copolymer-TNP-470 conjugate was injected, neither TNP-470 nor its known metabolites[36] were detected in the CSF. These results suggest that TNP-470-related neurotoxicity could be avoided when TNP-470 is conjugated to HPMA copolymer. Full body distribution and pharmacokinetics of free and conjugated TNP-470 in normal tissues, blood, urine and tumor analyzed by LC-MS/MS will be published separately.

Conclusions

Although a new departure in cancer therapy, several polymer-drug conjugates are already in early clinical trials[37]. These include HPMA copolymer-doxorubicin (PK1, FCE28068), 4PMA copolymer-paclitaxel (PNU 166945), HPMA copolymer-camptothecin, polyethylene glycol (PEG)-camptothecin, polyglutamic acid-paclitaxel, an HPMA copolymer-platinate (AP5280) and also an HPMA copolymer-doxorubicin conjugate bearing additionally galactosamine (PK2, FCE28069)[38]. Reduced toxicity and activity in chemotherapy refractory patients has been described. In phase I, PK1 displayed a maximum tolerated dose of 320 mg/m² (compared to 60 mg/m²: for free doxorubicin) and also showed antitumor activity[39]. Moreover, the clinical pharmacokinetics (PK1 $t_{1/2\alpha}$=1.8 h with no dose dependency of clearance compared to few minutes for free doxorubicin) were very similar to those reported in animals[25]. PK1 has proven ability to target solid tumors by the EPR effect[40] with concomitant renal elimination resulting in low blood levels within 1–5 h in animals and in humans[25,39].

Polymer-angiogenesis inhibitor conjugates can capitalize on the ability of macromolecules to target solid tumor tissue passively by the EPR effect[26] (similar to PK1). This effect occurs due to the poorly organized tumor vasculature[41] resulting in 'enhanced permeability' towards circulating molecules. The poor lymphatic drainage in tumor tissue leads to increased 'retention'. It is accepted that the main reason for the improved antitumor activity of the polymer-drug conjugates, with respect to the free drug, is tumor targeting as a result of this EPR effect[37]. Gly-Phe-Leu-Gly (SEQ ID NO: 1) polymer-TNP-470 linker used in this study was designed to permit intralysosomal TNP-470 liberation due to action of the lysosomal cysteine proteases[29]. In order to exert an antitumor effect, an active TNP-470 species must be released at the tumor site and interact with methionine aminopeptidase 2 (MetAP2) in endothelial cells. MetAP2 is one molecular target of TNP-470 that was recently identified, although the precise mechanism underlying its selective effect on the proliferation of endothelial cells is yet to be understood[42]. Therefore, the T/C values for the conjugate of 0.12–0.14 indicated that TNP-470, which was bound to the polymeric backbone during circulation, was released at the tumor site. The mechanism for release of a TNP-470 moiety involves cellular uptake, followed by enzymatic cleavage of the peptide linker within the lysosomes of endothelial cells. It is likely that some of the conjugate that accumulates in the tumor will be taken up by tumor cells. However, a higher concentration of TNP-470 will be needed to affect tumor cells (3-logs higher).

Many studies of angiogenesis inducers and inhibitors rely on in vitro or in vivo models as indicators of efficacy. However, as valuable as these models are, there are limitations to each one of these. Therefore, multiple assays used, involving both in vitro and in vivo assays, are at present the best way to minimize the problems inherent in any specific assay[43]. In this way, a proper evaluation and comparison between free and conjugated TNP-470, was achieved.

In summary, we have shown that tumor growth rate can be significantly reduced by systemic delivery of an antiangiogenic agent that is targeted to the tumor vasculature. In addition, this conjugate likely leads to reduced toxicity and does not cause weight loss in newborn and adult mice because, unlike the free form, it does not enter the CSF. The enhanced and long acting effect of the conjugate compared to that of the free TNP-470 (as described in the hepatectomy model), can be ascribed to increased accumulation in neovascularized tissues and to greater stability of the conjugate. Several components of this strategy contribute to its pronounced antitumor activity, which may facilitate future therapy in humans. First, the HPMA copolymer used in this study has multivalent side-chains, which make it possible to target high loading of TNP-470 or other drugs to angiogenic blood vessels due to the EPR effect. Second, it is feasible to conjugate an endothelial cell targeting moiety to those side-chains on the polymeric backbone[44]. Third, we emphasize that; (a) angiogenesis inhibitors suppress endothelial growth from inside the vascular lumen and may also traverse leaky tumor vessels; (b) the conjugate HPMA copolymer-TNP-470 provides prolonged exposure of the drug to endothelium; and (c) the conjugated TNP-470 cannot cross normal blood brain barrier. Lastly, polymers are less immunogenic than viral vectors and are known to decrease or even abrogate immunogenicity of bound proteins and to prolong circulation time[24,45]. Polymer-enzyme conjugates such as polyethylene glycol (PEG)-L-asparaginase (Oncaspar®) for the treatment of acute lymphoblastic leukemia have been FDA approved and has become commercially avaliable[46]. Therefore, it may be feasible to deliver therapeutic genes or proteins repeatedly to angiogenic blood vessels for sustained treatment of diseases that depend on angiogenesis and vascular remodeling. This study represents an example of how an effective angiogenesis inhibitor can be significantly improved and its toxicity decreased by conjugating it to a polymer.

EXAMPLE 2

Miles Assay:

One of the problems with angiogenesis-dependent diseases is increased vessel permeability (due to high levels of VPF) which results in edema and loss of proteins. A decrease in vessel permeability is beneficial in those diseases. We have found, using the Miles assay (Claffey et al., Cancer Res., 56: 172–181 (1996)), that free and bound TNP-470 block permeability. Briefly, a dye, Evans Blue, was injected i.v. to anesthesized mice. After 10 minutes, human recombinant $VEGF_{165}$ was injected intradermally into the back skin. Leakage of protein-bound dye was detected as blue spots on the underside of the back skin surrounding the injection site. After 20 minutes, mice were euthanized. Then, the skin was excised, left in formamide for 5 days to be extracted and the solution read at 620 nm. Putative angiogenesis inhibitors such as free and conjugated TNP-470 were injected daily 3 days prior to the VEGF challenge. The same was repeated on tumor-bearing mice to evaluate the effect of angiogenesis inhibitors on tumor vessel permeability.

Figure 6A:
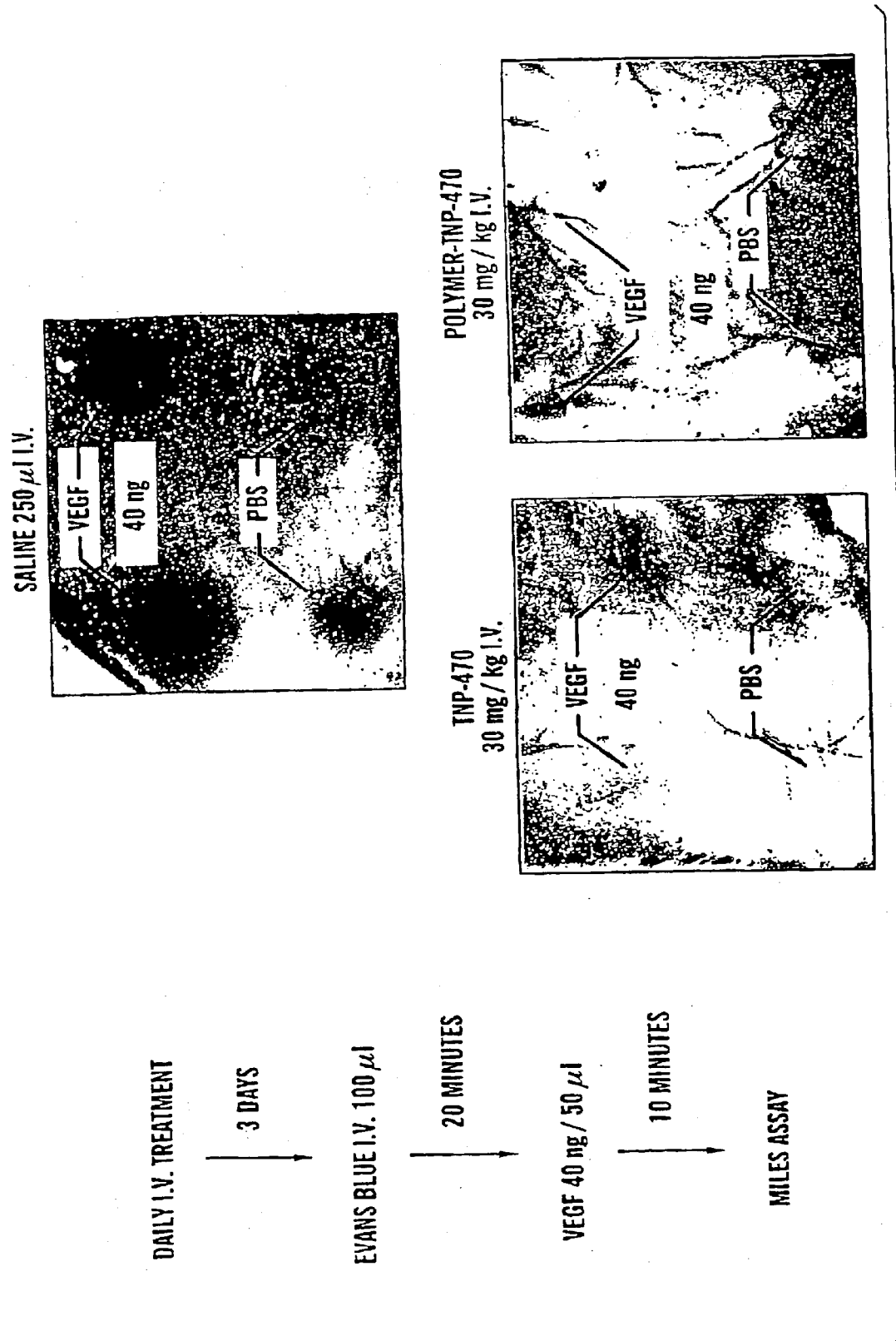
FIG. 6 shows the results of a Miles assay.
Figure 6B:
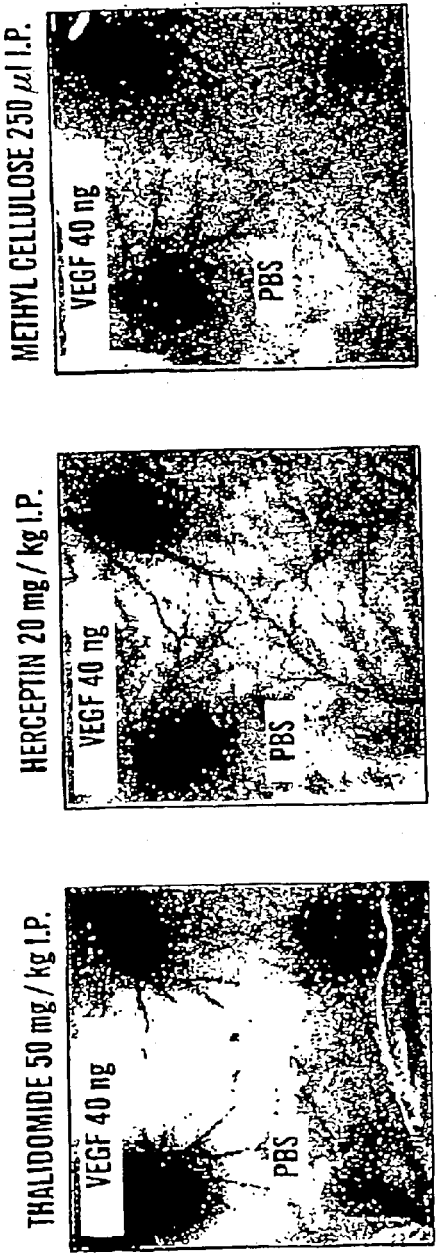
Figure 6B:
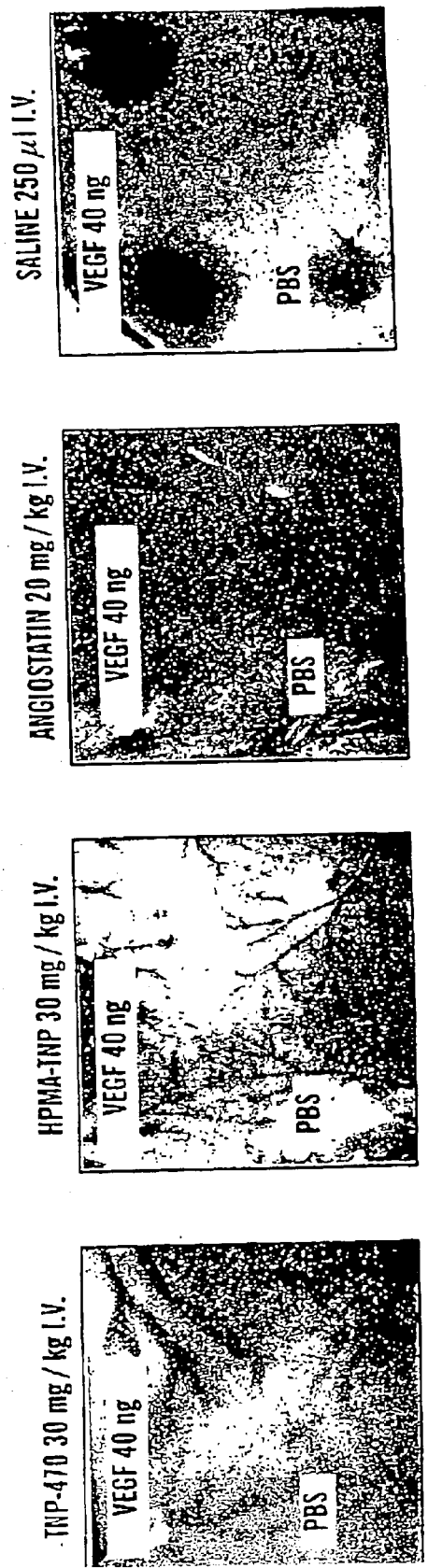

We have compared free and conjugated TNP-470 to other angiogenesis inhibitors in the Miles assay. We have found that free TNP-470 and HPMA copolymer-TNP-470 had similar inhibitory effect on VEGF induced vessel permeability as opposed to the control groups and indirect angiogenesis inhibitors such as Herceptin and Thalidomide (FIG. 6).

EXAMPLE 3

Figure 7:
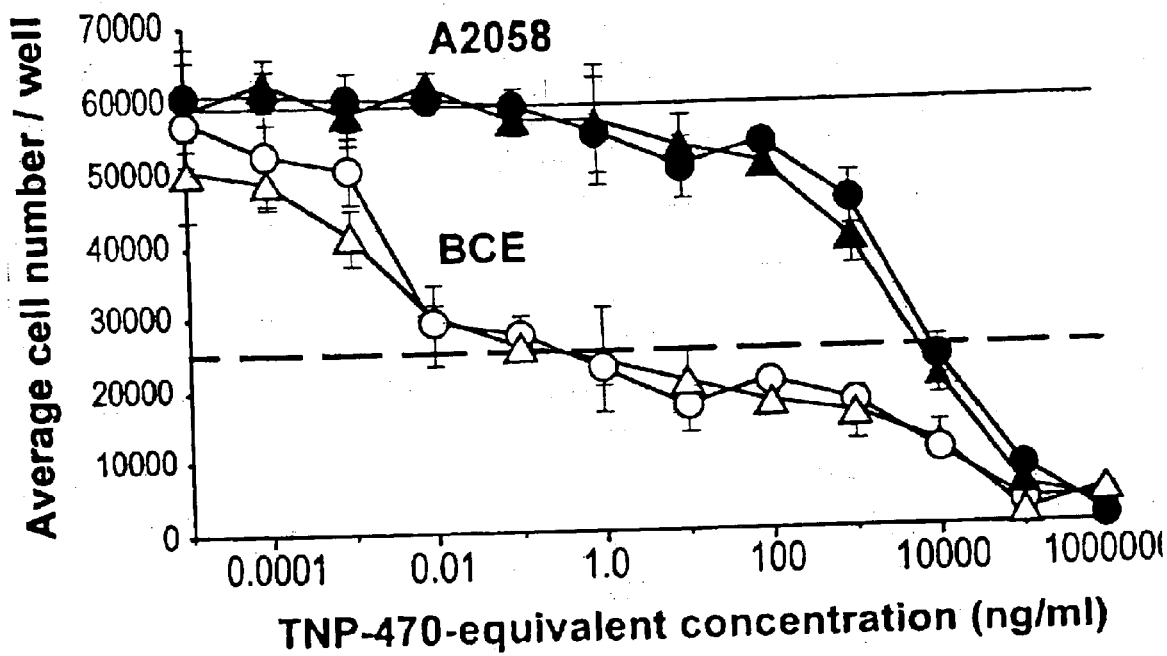
FIG. 7 shows the effect of TNP-470 on serum-induced cell proliferation. Inhibition of BCE (open symbols) and A2058 (closed symbols) cell proliferation in vitro after 72 h. TNP-470 (-●-) and HPMA copolymer-GFLG (SEQ ID NO: 1)-en-TNP-470 (-▲-) had similar cytostatic effect on bFGF-induced proliferation of endothelial cells at doses lower than 1 μg/ml and cytotoxic effect at doses higher than 1 μg/ml. The dotted line represents the proliferation of bFGF-induced BCE or serum-induced A2058 cells (—) and the solid line represents the BCE and A2058 cell proliferation in the absence of bFGF or serum, respectively ( - - - ).

TNP-470 and HPMA Copolymer-TNP 470 Selectively Inhibit Endothelial Cell Proliferation TNP-470 inhibited serum-induced proliferation (cytostatic effect) of A2058 melanoma cells beginning at 10 ng/ml (FIG. 7). At doses higher than 100 μg/ml TNP-470 was cytotoxic to these cells. TNP-470 was thus 4-logs more potent on endothelial cells than on tumor cells. On both cell lines, HPMA copolymer-TNP-470 conjugate had a similar effect on cell proliferation as the free TNP-470 (FIG. 7). HPMA copolymer alone was inert in vitro and in vivo (data not shown), in agreement with extensive data previously published on HPMA copolymers (reviewed in[51]).

Once Weekly Administration of HPMA Copolymer-TNP-470 Conjugate Inhibits Angiogenisis in the Liver Regeneration Model Free TNP-470 did not inhibit liver regeneration when injected at 60 mg/kg every four days or at a single injection of 120 mg/kg at the day of hepatectomy. However, HPMA copolymer-TNP-470 conjugate had an equivalent effect as the 30 mg/kg q.o.d. dosing schedule when given every 4 days (q.4.d.) at 60 mg/kg or at a single dose of 120 mg/kg on the day of hepatectomy. This suggests that the conjugate has a longer circulation time than the free TNP-470 in vivo and/or that the conjugate accumulates at the site of proliferating endothelial cells, leading to sustained release of TNP-470 from the polymer.

HPMA Copolymer-TNP-470 Conjugate Accumulates at Higher Concentration in Tumors and has a Longer Half-life in the Circulation than Free TNP-470

Figure 8A:
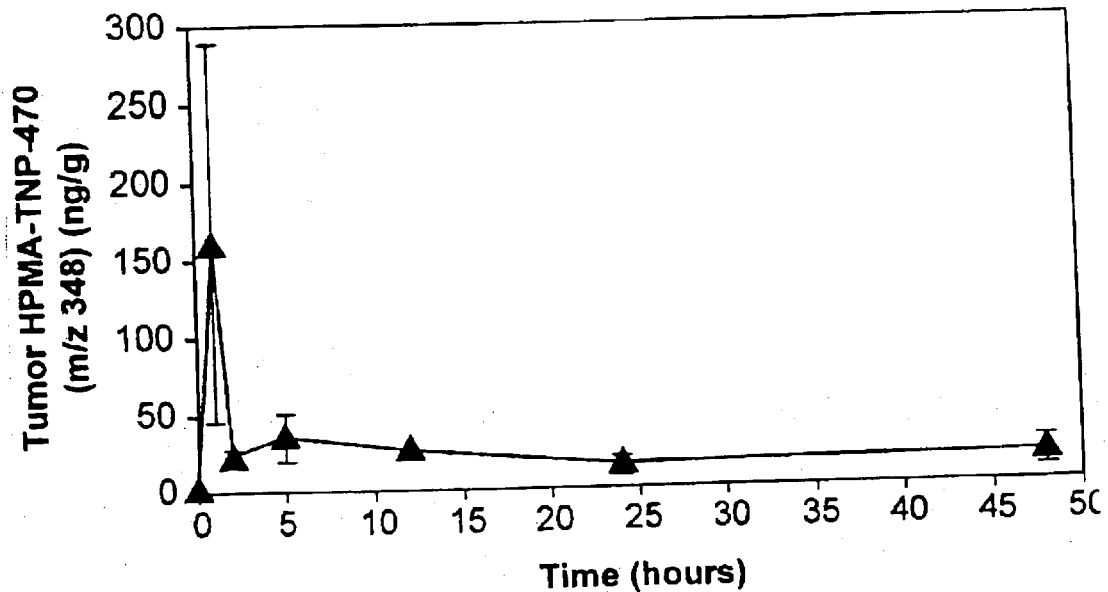
FIG. 8 shows HPMA copolymer-TNP-470 accumulation in tumors and serum. Panel 8(a) TNP-470 species extracted from tumors. Panel 8(b) TNP-470 extracted from serum. Free TNP-470 concentration was negligible at these time points. Values are mean±S.E., n-3 mice per group.
Figure 8B:
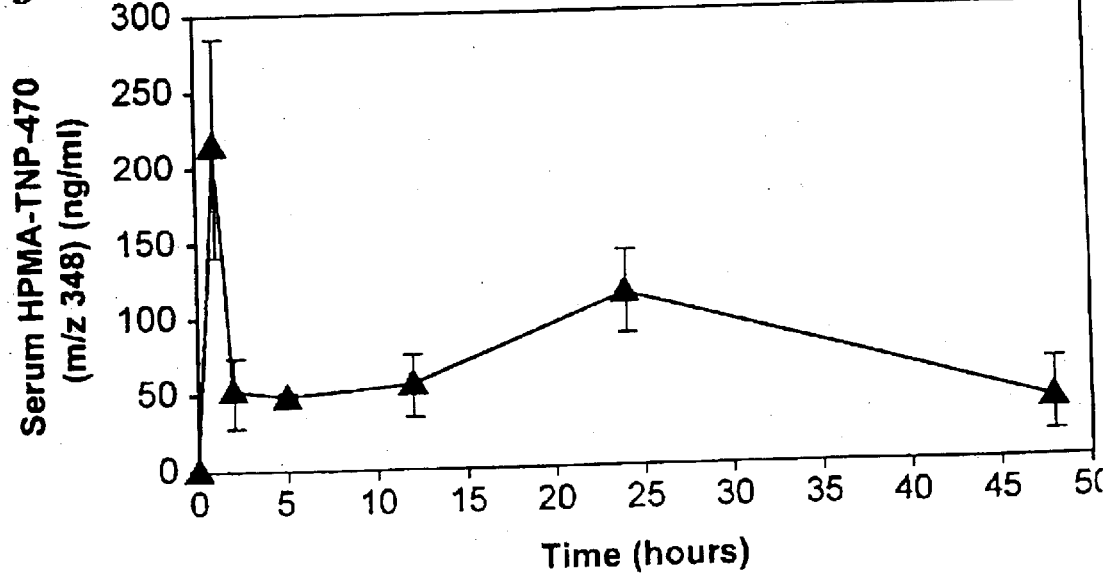

Free TNP-470 concentrations from serum specimens were only detected at the 1 and 2 h time points; with mean concentrations of 0.9, 1.7 ng/ml, respectively. There was no detectable TNP-470 in serum after then 2 h time point. Furthermore, no detectable concentrations of free TNP-470 were observed form tumor specimens at any given sample time points. However, TNP-470 active species, extracted sera and tumors of mice injected with HPMA copolymer-TNP-470, were present up to 48 h post injection (FIG. 8a and FIG. 8b). Half-life of circulating serum of the HPMA copolymer-TNP-470 mice sera is estimated up to 24 hours.

HPMA Copolymer-TNP-470 does not Affect Neurological Function

Figure 9A:
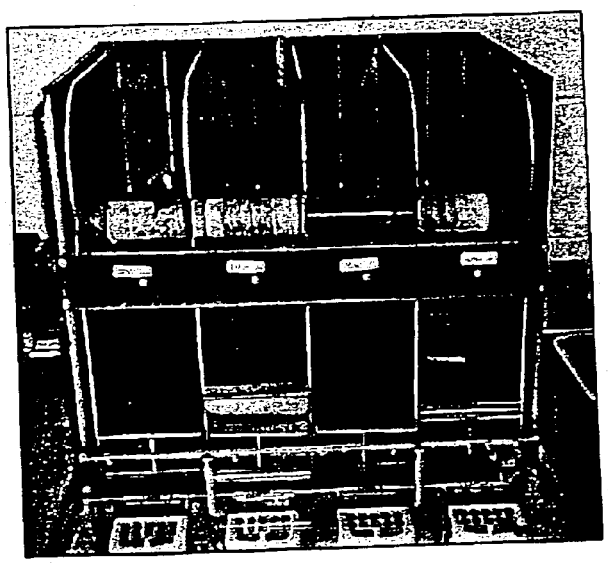
FIG. 9 shows the effects of TNP-470 and HPMA copolymer-TNP-470 on the motor skills of mice using the rotorod test. Panel 9(a) Mouse on a rotorod treadmill. Panel 9(b) Mice were treated with free TNP-470 (30 mg/kg q.o.d. s.c.; green columns), HPMA copolymer-TNP-470 (30 mg/kg q.o.d. s.c.; red columns), or saline (250 μl q.o.d. s.c.; blue columns) for 5 weeks. The mean time each group remained on the rotating rod is shown in the figure. Data are mean±S.E. n-5 mice per group. Panel 9(c) Body weight of mice treated with free TNP-470 (30 mg/kg q.o.d. s.c.) (-▲-), HPMA copolymer-TNP-470 (30 mg/kg q.o.d. s.c.) (-•-), or saline (250 μl q.o.d. s.c.) (-■-) for 5 weeks.
Figure 9B:
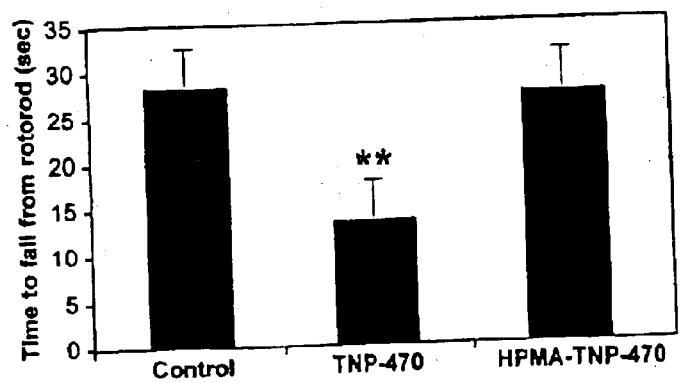
Figure 9C:
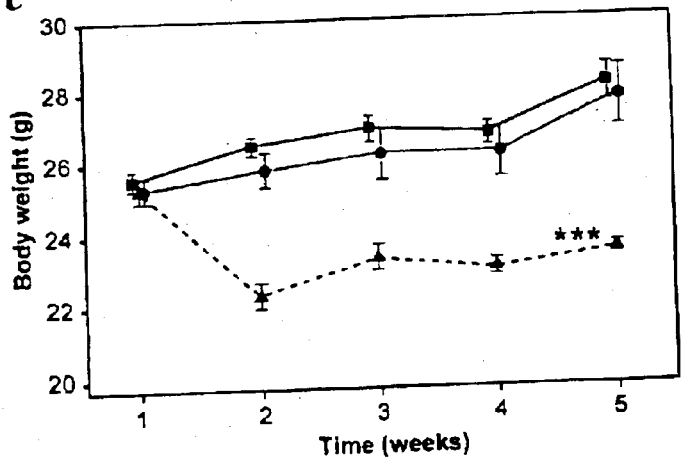

It has been shown that TNP-470 treatment results in severe ataxia and other symptoms of cerebellar dysfunction in humans[52]. Therefore, we tested the effects of TNP-470 and HPMA copolymer-TNP-470 on the motor skills of mice using the rotorod test, a classic assay for ataxia in rodents. Mice are placed on a rod that rotates at increasing speed, and the time that the mice remain on the rod is recorded (FIG. 9a). The performance of animals injected with HPMA copolymer-TNP-470 was indistinguishable from that of control mice, while mice injected with free TNP-470 remained on the rotating rod for significantly shorter times than the other 2 groups (P<0.03) (FIG. 9b). The experiment was repeated every day for 5 consecutive days with similar results (data not shown). Mice treated with free TNP-470 lost weight, while mice treated with HPMA copolymer-TNP-470 gained weight similar to control mice (P<0.01) (FIG. 9c). These results indicate that while TNP-470 injection leads to ataxia, HPMA copolymer-TNP-470 does not affect the motor coordination of mice. Interestingly, there were no visible neurohistological alterations in the mice injected with free TNP-470 (data not shown). This indicates that free TNP-470 induces neuronal dysfunction but does not affect neuronal survival, consistent with the observation that the neurological side effects in humans are reversible[52].

Conclusion

Several polymer-cytotoxic drug conjugates are already in early clinical trials[53]. These include HPMA copolymer-doxorubicin (PK1, FCE28068), HPMA copolymer-paclitaxel (PNU 166945), HPMA copolymer-camptothecin, polyethylene glycol (PEG)-camptothecin, polyglutamic acid-paclitaxel, and HPMA copolymer-platinate (AP5280) and also an HPMA copolymer-doxorubicin conjugate bearing additionally galactosamine as a targeting moiety to the liver (PK2, FCE28069)[51]. Reduced toxicity and activity in chemotherapy refractory patients has been described. In phase I, PK1 displayed a maximum tolerated dose of 320 mg/m$^2$ (compared to 60 mg/$^2$ for free doxorubicin) and also showed antitumor activity[54]. Moreover, the clinical pharmacokinetics (PK1 $t_{1/2a}$=1.8 h with no dose dependency of clearance compared to a few minutes for free doxorubicin) were very similar to those reported in animals[55]. PK1 has proven ability to target solid tumors by the EPR effect[56] with concomitant renal elimination resulting in low blood levels within 1–5 h in animals and in humans[54,55].

In order to exert an antitumor effect, an active TNP-470 species must be released at the tumor site and interact with methionine aminopeptidase 2 (MetAP2) in endothelial cells. MetAP2 is one molecular target of TNP-470 that was recently identified, although the precise mechanism underlying its selective effect on the proliferation of endothelial cells is yet to be understood[57]. Therefore, the T/C values for the conjugate of 0.12–0.14 indicated that TNP-470, which was bound to the polymeric backbone during circulation, was released at the tumor site in an active form. The mechanism for release of a TNP-470 moiety involves cellular uptake, followed by enzymatic cleavage of the peptide linker within the lysosomes of endothelial cells. It is likely that some of the conjugate that accumulates in the tumor will be taken up by tumor cells.

There are two main reasons why the conjugate should affect endothelial cells in tumors and regenerating livers, but not affect those of the neonate and the blood brain barrier and other quiescent vessels. The first reason is that TNP-470 only affects proliferating endothelial cells. TNP-470 is known to induce p53 activation through a unique mechanism in endothelial cells leading to an increase in cyclin-dependent kinase inhibitor p21$^{CIP/WAF}$ expression and subsequent growth arrest[58,59]. p21 prevents the entry of the cells in S phase by inhibiting the activity of CDK2. Jing-Ruey et al., showed that TNP-470 selectively arrests the growth of endothelial cells, but not non-endothelial cells by activating p53 and inducing p21 only in endothelial cells. Furthermore, Zhang et al. showed that TNP-470 did not affect contact-inhibited endothelial cells in the G0–G1 phase.

The liver endothelial cells are sensitive to TNP-470 in our experiment only during the 8 day period of endothelial proliferation in regenerating liver[60,61]. In contrast, the endothelial cells lining the blood brain barrier are not proliferating. However, the unresponsiveness of quiescent, non-proliferating endothelial cells lining the blood brain barrier does not prevent the diffusion of free TNP-470 to the brain tissue. The most likely mechanism by which free TNP-470 is neurotoxic is by directly affecting neuronal function. However, the mechanism for this is still unknown. The fact that the neurological effects of free TNP-470 in humans are rapidly reversible upon discontinuation of TNP-470 treatment suggests that TNP-470 does not produce long-term neuronal degeneration.

The second reason that the conjugate shows selective effects against tumor and regenerating liver endothelial cells, is that the conjugate circulates for a longer time than TNP-470 and accumulates selectively at higher concentration in tissues where vessels are leaky. On the other hand, free TNP-470 can diffuse from normal vessels homogenously throughout the body. Hence, the proliferating endothelial cells in the leaky environments of the tumor and the regenerating liver will be exposed for a much longer time to TNP-470 when it is conjugated to the polymer due to its size and structure (enhanced permeability and retention (EPR) effect).

Seymour et al., have shown that the HPMA copolymer conjugates are internalized into cells via slow fluid phase pinocytosis[62]. Hence, these HPMA conjugates need to be present in the vessel microenvironment for a period of time in order to internalize into the endothelial cells. In short, HPMA-TNP-470 conjugate requires both the leaky environment and proliferating endothelial cells to be effective.

The references cited throughout the specification are incorporated herein by reference.

References

1. Folkman, J. Angiogenesis. in *Harrison's Textbook of Internal Medicine* (eds. Braunwald, E. et al.) 517–530 (McGraw Hill, New York, 2001).
2. Hanahan, D. & Folkman, J. Patterns and emerging mechanisms of the angiogenic switch during tumorigenesis. *Cell* 86, 353–64 (1996).
3. Volpert, O. V. et al. Id1 regulates angiogenesis through transcriptional repression of thrombospondin-1. *Cancer Cell* 2, 473–483 (2002).
4. Folkman, J. Tumor angiogenesis. in *Cancer Medicine* (eds. Holland, J. et al.) 132–152 (B. C. Decker Inc., Ontario, Canada, 2000).
5. Lyden, D. et al. Id1 and Id3 are required for neurogenesis, angiogenesis and vascularization of tumour xenografts. *Nature* 401, 670–7 (1999).
6. Streit, M. et al. Thrombospondin-2: a potent endogenous inhibitor of tumor growth and angiogenesis. *Proc Natl Acad Sci USA* 96, 14888–93 (1999).
7. Chin, L. et al. Essential role for oncogenic Ras in tumour maintenance. *Nature* 400, 468–72 (1999).
8. Tabone, M. D. et al. Are basic fibroblast growth factor and vascular endothelial growth factor prognostic indicators in pediatric patients with malignant solid tumors? *Clin Cancer Res* 7, 538–43 (2001).
9. Yao, Y. et al. Prognostic value of vascular endothelial growth factor and its receptors Flt-1 and Flk-1 in astrocytic tumours. *Acta Neurochir (Wien)* 143, 159–66 (2001).

10. Yuan, A. et al. Aberrant p53 expression correlates with expression of vascular endothelial growth factor mRNA and interleukin-8 mRNA and neoangiogenesis in non-small-cell lung cancer. *J Clin Oncol* 20, 900–910 (2002).
11. Ingber, D. et al. Synthetic analogues of fumagillin that inhibit angiogenesis and suppress tumour growth. *Nature* 348, 555–7 (1990).
12. Antoine, N. et al. AGM-1470, a potent angiogenesis inhibitor, prevents the entry of normal but not transformed endothelial cells into the G1 phase of the cell cycle. *Cancer Res* 54, 2073–6 (1994).
13. Folkman, J. Tumor angiogenesis. in *Accomplishments in cancer research* (eds. Wells, S. J. & Sharp, P.) 32–44 (Lippincott Williams & Wilkins, New York, 1998).
14. Kudelka, A. P., Verschraegen, C. F. & Loyer, E. Complete remission of metastatic cervical cancer with the angiogenesis inhibitor TNP-470. *N Engl J Med* 338, 991–2 (1998).
15. Kudelka, A. P. et al. A phase I study of TNP-470 administered to patients with advanced squamous cell cancer of the cervix. *Clin Cancer Res* 3, 1501–5 (1997).
16. Bhargava, P. et al. A Phase I and pharmacokinetic study of TNP-470 administered weekly: to patients with advanced cancer. *Clin Cancer Res* 5, 1989–95 (1999).
17. Herbst, R. S. et al. Safety and pharmacokinetic effects of TNP-470, an angiogenesis inhibitor, combined with paclitaxel in patients with solid tumors: evidence for activity in non-small-cell lung cancer. *J Clin Oncol* 20, 4440–7 (2002).
18. Kim, E. S. & Herbst, R. S. Angiogenesis inhibitors in lung cancer. *Curr Oncol Rep* 4, 325–33 (2002).
19. Stadler, W. M. et al. Multi-institutional study of the angiogenesis inhibitor TNP-470 in metastatic renal carcinoma. *J Clin Oncol* 17, 2541–5 (1999).
20. Logothetis, C. J. et al. Phase I trial of the angiogenesis inhibitor TNP-470 for progressive androgen-independent prostate cancer. *Clin Cancer Res* 7, 1198–203 (2001).
21. Rupnick, M. A. et al. Adipose tissue mass can be regulated through the vasculature. *Proc Natl Acad Sci USA* 99, 10730–5 (2002).
22. Schoof, D. D. et al. The influence of angiogenesis inhibitor AGM-1470 on immune system status and tumor growth in vitro. *Int J Cancer* 55, 630–5 (1993).
23. Nagabuchi, E., VanderKolk, W. E., Une, Y. & Ziegler, M. M. TNP-470 antiangiogenic therapy for advanced murine neuroblastoma. *J. Pediatr Surg* 32, 287–93 (1997).
24. Rihova, B. et al. Biocompatibility of N-(2-hydroxypropyl) methacrylamide copolymers containing adriamycin. Immunogenicity, and effect on haematopoietic stem cells in bone marrow in vivo and mouse splenocytes and human peripheral blood lymphocytes in vitro. *Biomaterials* 10, 335–42. (1989).
25. Seymour, L. W., Ulbrich, K., Strohalm, J., Kopecek, J. & Duncan, R. The pharmacokinetics of polymer-bound adriamycin. *Biochem Pharmacol* 39, 1125–31 (1990).
26. Maeda, H., Wu, J., Sawa, T., Matsumura, Y. & Hori, K. Tumor vascular permeability and the EPR effect in macromolecular therapeutics: a review. *J Control Release* 65, 271–84 (2000).
27. Duncan, R., Coatsworth, J. K. & Burtles, S. Preclinical toxicology of a novel polymeric antitumour agent: HPMA copolymer-doxorubicin (PK1). *Hum Exp Toxicol* 17, 93–104 (1998).
28. Satchi-Fainaro, R. Targeting tumour vasculature: Reality or a dream? *J Drug Targeting* 10, 529–533 (2002).
29. Duncan, R., Cable, H. C., Lloyd, J. B., Rejmanova, P. & Kopecek, J. Polymers containing enzymatically degradable bonds, 7. Design of oligopeptide side chain in poly N-(2-hydroxypropyl)methacrylamide copolymers to promote efficient degradation by lysosomal enzymes. *Makromol Chem* 184, 1997–2008 (1984).
30. Foekens, J. A. et al., Prognostic significance of cathepsins B and L in primary human breast cancer. *J Clin Oncol* 16, 1013–21 (1998).
31. Gianasi, E. et al. HPMA copolymer platinates as novel antitumour agents: in vitro properties, pharmacokinetics and antitumour activity in vivo. *Eur J Cancer* 35, 994–1002 (1999).
32. Kusaka, M. et al. Cytostatic inhibition of endothelial cell growth by the angiogenesis inhibitor TNP-470 (AGM-1470). *Br J Cancer* 69, 212–6 (1994).
33. Greene, A. K. et al. Endothelial directed hepatic regeneration after partial hepatectomy. *Annals of Surgery* in press (2003).
34. Drixler, T. A. et al. Liver regeneration is an angiogenesis-associated phenomenon. *Ann Surg* 236, 703–12 (2002).
35. Klein, S. A., Bond, S. J., Gupta, S. C., Yacoub, O. A. & Anderson, G. L. Angiogenesis inhibitor TNP-470 inhibits murine cutaneous wound healing. *J Surg Res* 82, 268–74 (1999).
36. Whalen, C. T., Hanson, G. D., Putzer, K. J., Mayer, M. D. & Mulford, D. J. Assay of TNP-470 and its two major metabolites in human plasma by high-performance liquid chromatography-mass spectrometry. *J Chromatogr Sci* 40, 214–8 (2002).
37. Brocchini, S. & Duncan, R. Polymer-Drug conjugates: drug release from pendent linkers. in *Encyclopaedia of controlled release* (ed. Mathiovitz, E.) 786–816 (New York: Wiley, 1999).
38. Duncan, R. et al. Polymer-drug conjugates, PDEPT and PELT: basic principles for design and transfer from the laboratory to clinic. *J Control Release* 74, 135–46 (2001).
39. Vasey, P. A. et al. Phase I clinical and pharmacokinetic study of PK1 [N-(2-hydroxypropyl)methacrylamide copolymer doxorubicin]: first member of a new class of chemotherapeutic agents-drug-polymer conjugates. Cancer Research Campaign Phase I/II Committee. *Clin Cancer Res* 5, 83–94 (11999).
40. Seymour, L. W. et al. Tumour tropism and anti-cancer efficacy of polymer-based doxorubicin prodrugs in the treatment of subcutaneous murine B16F10 melanoma. *Br J Cancer* 70, 636–41 (1994).
41. Dvorak, H. F., Nagy, J. A., Dvorak, J. T. & Dvorak, A. M. Identification and characterization of the blood vessels of solid tumors that are leaky to circulating macromolecules. *Am J Pathol* 133, 95–109 (1988).
42. Griffith, E. C. et al. Methionine aminopeptidase (type 2) is the common target for angiogenesis inhibitors AGM-1470 and ovalicin. *Chem Biol* 4, 461–71 (1997).
43. Auerbach, R., Akhtar, N., Lewis, R. L. & Shinners, B. L. Angiogenesis assays: problems and pitfalls. *Cancer Metastasis Rev* 19, 167–72 (2000).
44. Seymour, L. W. et al. Hepatic drug targeting: phase I evaluation of polymer-bound doxorubicin. *J Clin Oncol* 20, 1668–76 (2002).

45. Francis, G. E., Delgado, C. & Fisher, D. PEG-modified proteins. in *Stability of proteins pharmaceuticals* (Part B) (ed. Ahern T J, M. M.) 235–263 (Plenum Press, New York, 1992).
46. Ho, D. H. et al. Clinical pharmacology of polyethylene glycol-L-asparaginase. *Drug Metab Dispos* 14, 349–52 (1986).
47. O'Reilly, M. S. et al. Angiostatin: a novel angiogenesis inhibitor that mediates the suppression of metastases by a Lewis lung carcinoma. *Cell* 79, 315–28 (1994).
48. Folkman, J., Haudenschild, C. C. & Zetter, B. R. Long-term culture of capillary endothelial cells. *Proc Natl Acad Sci USA* 76, 5217–21 (1979).
49. Paxinos, J. & Franklin, K. B. J. *The Mouse Brain in Stereotaxic Coordinates*, (Academic Press, 2001).
50. Waynforth, H. B. Routes and methods of administration, Intracerebral injection. in *Experimental and Surgical technique in the rat*, Vol. 2.9 34–36 (Academic Press, London, 1980).
51. Duncan, R et al. Polymer-drug conjugates, PDEPT and PELT: basic principles for design and transfer from the laboratory to clinic. *J Control Release* 74, 135–46 (2001).
52. Bhargava, P. et al. A Phase I and pharmacokinetic study of TNP-470 administered weekly to patients with advanced cancer. *Clin Cancer Res* 5, 1989–95 (1999).
53. Brocchini, S. & Duncan, R. Polymer-Drug conjugates: drug release from pendent linkers. In *Encyclopaedia of controlled release* (ed. Mathiovitz, E.) 786–816 (New York: Wile, 1999).
54. Vasey, P. A. et al. Phase 1 clinical and pharmacokinetic study of PK1 [N-2(2-hydroxypropyl) methacrylamide copolymer doxorubicin]: first member of a new class of chemotherapeutic agents-drug-polymer conjugates. Cancer Research Campaign Phase I/II Committee. *Clin Cancer Res* 5, 83–94 (1999).
55. Seymour, L. W., Ulbrich, K.,. Strohalm, J., Kopecek, J. & Duncan, R. The pharmacokinetics of polymer-bound adriamycin. *Biochem Pharmacol* 39, 1125–31 (1990).
56. Seymour, L. W. et al. Tumour tropism and anti-cancer efficacy of polymer-based doxorubicin prodrugs in the treatment of subcutaneous murine B16F10 melanoma. *Br J Cancer* 70, 636–41 (1994).
57. Griffith, E. C. et al. Methionine aminopeptidase (type 2) is the common target for angiogenesis inhibitors AGM-1470 and ovalicin. *Chem Biol* 4, 461–71 (1997).
58. Yeh, J. R., Mohan, R. & Crews, C. M. The antiangiogenic agent TNP-470 requires p53 and p21CIP/WAF for endothelial cell growth arrest. *Proc Natl Acad Sci USA* 97, 12782–7 (2000).
59. Zhang, Y., Griffith, E. C., Sage, J., Jacks, T. & Liu, J. O. Cell cycle inhibition by the anti-angiogenic agent. TNP-470 is mediated by p53 and p21WAF1/CIP1. *Proc Natl Acad Sci USA* 97 6427–32 (2000).
60. Greene, A. K. et al. Endothelial-directed hepatic regeneration after partial hepatectomy. *Ann Surg* 237, 530–5 (2003).
61. Drixler, T. A. et al. Liver regeneration is an angiogenesis-associated phenomenon. *Ann Surg* 236, 703–12 (2002).
62. Seymour, L. W. et al. N-2(2-hydroxypropyl) methacrylamide copolymers targeted to the hepatocyte galactose-receptor: pharmacokinetics in DBA2 mice. *Br J Cancer* 63, 859–66(1991).

Although the foregoing invention has been described in some detail by way of illustration and example for the purposes of clarity of understanding, one skilled in the art will easily ascertain that certain changes and modifications may be practiced without departing from the spirit and scope of the appended claims.

What is claimed is:

1. A compound of the formula

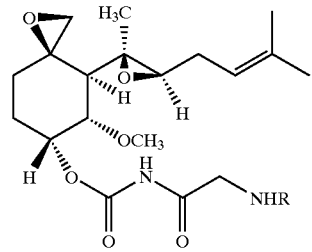

wherein R is $(CH_2)_nR'$, where n is 1 to 3, R' is $NH_2$, OH or SH, or a pharmaceutically acceptable salt thereof.

2. The compound of claim 1, wherein R' is $(CH_2)_2NH_2$.

3. A method of inhibiting angiogenesis in a mammal having undesired angiogenesis comprising administering an effective amount of the compound of claim 1.

* * * * *

UNITED STATES PATENT AND TRADEMARK OFFICE
CERTIFICATE OF CORRECTION

PATENT NO. : 6,949,584 B2
APPLICATION NO. : 10/783986
DATED : September 27, 2005
INVENTOR(S) : Ronit Satchi-Fainaro and Judah Folkman It is certified that error appears in the above-identified patent and that said Letters Patent is hereby corrected as shown below:

Col. 22, line 62
Replace "2. The compound of claim 1, wherein R' is $(CH_2)_2NH_2$."
with --2. The compound of claim 1, wherein R is $(CH_2)_2NH_2$.--.

Signed and Sealed this

Twelfth Day of September, 2006

JON W. DUDAS
*Director of the United States Patent and Trademark Office*